US007306783B2

(12) United States Patent
Piwnica-Worms

(10) Patent No.: US 7,306,783 B2
(45) Date of Patent: *Dec. 11, 2007

(54) MEMBRANE-PERMEANT PEPTIDE COMPLEXES FOR MEDICAL IMAGING, DIAGNOSTICS, AND PHARMACEUTICAL THERAPY

(75) Inventor: David Piwnica-Worms, Ladue, MO (US)

(73) Assignee: Washington University, St. Louis, MO (US)

( * ) Notice: Subject to any disclaimer, the term of this patent is extended or adjusted under 35 U.S.C. 154(b) by 310 days.

This patent is subject to a terminal disclaimer.

(21) Appl. No.: 10/368,280

(22) Filed: Feb. 18, 2003

(65) Prior Publication Data

US 2003/0219375 A1 Nov. 27, 2003

Related U.S. Application Data

(62) Division of application No. 09/557,465, filed on Apr. 25, 2000, now Pat. No. 6,589,503.

(51) Int. Cl.
*A61K 51/00* (2006.01)
*A61M 36/14* (2006.01)

(52) U.S. Cl. ............... 424/1.69; 424/1.11; 424/1.65; 424/9.1; 530/300

(58) Field of Classification Search ............ 424/1.11, 424/1.65, 1.69, 9.1; 530/300
See application file for complete search history.

(56) References Cited

U.S. PATENT DOCUMENTS

| | | | |
|---|---|---|---|
| 4,452,774 A | 6/1984 | Jones et al. | |
| 4,526,714 A | 7/1985 | Feijen et al. | |
| 4,554,101 A | 11/1985 | Hopp | |
| 4,988,496 A | 1/1991 | Srinivzsen et al. | |
| 5,135,736 A * | 8/1992 | Anderson et al. | 424/1.49 |
| 5,169,933 A | 12/1992 | Anderson et al. | |
| 5,403,574 A | 4/1995 | Piwnica-Worms | |
| 5,652,122 A | 7/1997 | Frankel et al. | |
| 5,670,133 A * | 9/1997 | Zamora | 424/9.1 |
| 5,670,617 A | 9/1997 | Frankel et al. | |
| 5,674,980 A | 10/1997 | Frankel et al. | |
| 5,747,641 A | 5/1998 | Frankel et al. | |
| 5,804,604 A | 9/1998 | Frankel et al. | |
| 5,846,743 A | 12/1998 | Janmey et al. | |
| 6,348,185 B1 * | 2/2002 | Piwnica-Worms | 424/1.69 |
| 6,589,503 B1 * | 7/2003 | Piwnica-Worms | 424/1.69 |
| 2003/0219375 A1 * | 11/2003 | Piwnica-Worms | 424/1.11 |

FOREIGN PATENT DOCUMENTS

| | | |
|---|---|---|
| CA | 2094658 | 10/1993 |
| EP | 0213523 | 3/1987 |
| EP | 0359347 | 3/1990 |
| WO | WO 91/09958 | 7/1991 |
| WO | WO 94/04686 | 3/1994 |
| WO | WO 98/52614 | 11/1998 |
| WO | WO 99/09056 | 2/1999 |
| WO | WO 99/67284 | 12/1999 |
| WO | WO 01/82975 A3 | 11/2001 |

OTHER PUBLICATIONS

Vives et al (Dec. 1997), Letters in Peptide Science, vol. 4, pp. 429-436.*
U.S. Appl. No. 60/082,402, filed Apr. 20, 1998.
U.S. Appl. No. 60/111,701, filed Dec. 10, 1998.
U.S. Appl. No. 60/122,757, filed Feb. 28, 1999.
Akiyama et al., "Isolation and Genetic Characterization of Human KB Cell Lines Resistant to Multiple Drugs," Somatic Cell and Molecular Genetics, 1985, pp. 117-126, vol. 11.
Albericio et al., "Use of Onium Salt-Based Coupling Reagents in Peptide Synthesis," J. Org. Chem., 1998, pp. 9678-9683, vol. 63.
Anderson et al., "Tumor Cell Retention of Antibody Fab Fragments is Enhanced by an Attached HIV Tat Protein-Derived Peptide," Biochem. Biophys. Res. Comm., 1993, pp. 876-884, vol. 194.
Arano et al., "Chemical Design of Radiolabeled Antibody Fragments for Low Renal Radioactivity Levels," Cancer Res., 1999, pp. 128-134, vol. 39.
Arpicco et al., "New Coupling Reagents for the Preparation of Disulfide Cross-Linked Conjugates with Increased Stability," Bioconjugate Chem., 1997, pp. 327-337, vol. 8.
Ashkenazi et al., "Death Receptors: Signaling and Modulation," Science, 1998, pp. 1305-1308, vol. 281.
Avrameas et al., "Polyreactive anti-DNA Monoclonal Antibodies and a Derived Peptide as Vectors for the Intracytoplasmic and Intranuclear Translocation of Macromolecules," Proc. Natl. Acad. Sci. USA, 1998, pp. 5601-5606, vol. 95.
Babich et al., "Effect of "Co-ligand" on the Biodistribution of $^{99m}$Tc-labeled Hydrazino Nicotinic Acid Derivatized Chemotactic Peptides," Nucl. Med. Biol., 1995, pp. 25-30, vol. 22.
Baum et al., "Initial Clinical Results with Technetium-99m-Labeled LL2 Monoclonal Antibody Fragment in the Radioimmunodetection of B-Cell Lymphomas," Cancer, 1994, pp. 896-899, vol. 73.
Behr et al., "Comparison of Complete Versus Fragmented Technetium-99m-Labeled Anti-CEA Monoclonal Antibodies for Immunoscintigraphy in Colorectal Cancer," J. Nuclear Med., 1995, pp. 430-441, vol. 36.
Beyer et al., "Synthesis and in Vitro Efficacy of Transferrin Conjugates of the Anticancer Drug Chlorambucil," J. Med. Chem., 1998, pp. 2701-2708, vol. 41.
Blankenberg et al., "In Vivo Detection and Imaging of Phosphatidylserine Expression During Programmed Cell Death," Proc. Natl. Acad. Sci. USA, 1998, pp. 6349-6354, vol. 95.

(Continued)

*Primary Examiner*—Dameron L. Jones
(74) *Attorney, Agent, or Firm*—Sonnenschein Nath & Rosenthal LLP

(57) ABSTRACT

Methods and compositions for medical imaging, evaluating intracellular processes and components, radiotherapy of intracellular targets, and drug delivery by the use of novel cell membrane-permeant peptide conjugate coordination and covalent complexes having target cell specificity are provided. Kits for conjugating radionuclides and other metals to peptide coordination complexes are also provided.

50 Claims, 8 Drawing Sheets

OTHER PUBLICATIONS

Blomberg et al., "Terbium and Rhodamine and Labels in a Homogeneous Time-Resolved Fluorometric Energy Transfer Assay of the β Subunit of Human Chorionic Gonadotropin in Serum," Clinical Chem., 1999, pp. 855-861, vol. 45.

Bosch et al., "Characterization of Functional Assays of Multidrug Resistance P-Glycoprotein Transport Activity," Leukemia, 1997, pp. 1131-1137, vol. 11.

Buijs et al., "Dosimetric Evaluation of Immunoscintigraphy Using Indium-111-Labeled Monoclonal Antibody Fragments in Patients with Ovarian Cancer," J. Nuclear Med., 1992, pp. 1113-1120, vol. 33.

Choi et al., "Bodistribution of $^{18}$F- and $^{123}$I-Labeled Anti-Tac Disulfide-Stabilized Fv Fragments in Nude Mice with Interleukin 2α Receptor-Positive Tumor Xenografts," Cancer Res., 1995, pp. 5323-5329, vol. 55.

Deguchi et al., "Retention of Biologic Activity of Human Epidermal Growth Factor Following Conjugation to a Blood-Brain Barrier Drug Delivery Vector Via an Extended Poly(ethylene glycol) Linker," Bio. Chem., 1999, pp. 32-37, vol. 10.

DeRossi et al., "Trojan Peptides: The Penetratin System for Intracellular Delivery," Cell Biol., 1998, pp. 84-87, vol. 8.

DeRossi et al., "Cell Internalization of the Third Helix of the Antennapedia Homeodomain is Receptor-Independent," J. Biol. Chem., 1996, pp. 18188-18193, vol. 271.

Dirven et al., "Glutathione Conjugation of Alkylating Cytostatic Drugs with a Nitrogen Mustard Group and the Roleof Glutathion S-Transferases," Chem. Res. Toxicol., 1996, pp. 351-360, vol. 9.

Dischino et al., "Relationship Between Lipophilicity and Brain Extraction of C-II-Labeled Radiopharmaceuticals," J. Nuclear Medicine, 1983, pp. 1030-1038, vol. 24.

Drouillat et al., "Novel Liposaccharide Conjugates for Drug and Peptide Delivery," J. Pharm. Sci., 1998, pp. 25-30, vol. 87.

Eckelman, "Radiolabeling with Technetium-99m to Study High-Capacity and Low-Capacity Biochemical Systems," European J. Nuclear Med., 1995, pp. 249-263, vol. 22.

Efthymiadis et al., "The HIV-1 Tat Nuclear Localization Sequence Confers Nuclear Import Properties," J. Biol. Chem., 1998, pp. 1623-1628, vol. 273.

Elliott et al., "Intercellular Trafficking and Protein Delivery by a Herpesvirus Structural Protein," Cell, 1997, pp. 223-233, vol. 88.

Enari et al., "Sequential Activation of ICE-like and CPP32-like Proteases During Fas-Mediated Apoptosis," Nature, 1996, pp. 723-726, vol. 380.

Engelstad et al., "Contrast Agents," Introduction, pp. 161-181, Chapter 9, 1951.

Evan et al., "A Matter of Life and Cell Death," Science, 1998, pp. 1317-1322, vol. 281.

Fahraeus et al., "Inhibition of pRb phosphorylatoin and Cell-Cycle Progression by a 20-Residue Peptide Derived from p16$^{CDKN2/INK4A}$," Current Biology, 1996, pp. 84-91, vol. 6.

Fawell et al., "Tat-Mediated Delivery of Heterologous Proteins in Cells," Proc. Natl. Acad. Sci. USA, 1994, pp. 664-668, vol. 91.

Fernandes-Alnemri et al., "In Vitro Activation of CPP32 and Mch3 by Mch4, a Novel Human Cysteine Protease Containing Two FADD-like Domains," Proc. Natl. Acad. Sci. USA, 1996, pp. 7464-7469, vol. 93.

Fisher, "Apoptosis in Cancer Therapy: Crossing the Threshold," Cell, 1994, pp. 539-542, vol. 78.

Frankel et al., "Cellular Uptake of the Tat Protein from Human Immunodeficiency Virus," Cell, 1988, pp. 1189-1193, vol. 55.

Frisch et al., "Synthesis of Short Polyoxyethylene-Based Heterobifunctional Cross-Linking Reagents. Application to the Coupling of Peptides to Liposomes," Bioconjugate Chem., 1996, pp. 180-186, vol. 7.

Fulda et al., "The CD95 (APO-1Fas) System Mediates Drug-Induced Apoptosis in Neuroblastoma Cells," Cancer Res., 1997, pp. 3823-3829, vol. 57.

Fuller, "The Steroid Receptor Superfamily: Mechanisms of Diversity," FASEB J., 1991, pp. 3092-3099, vol. 5.

Garcia et al., "Functional Domains Required for Tat-Induced Transcriptional Activation of the HIV-1 Long Terminal Repeat," The EMBO J., 1988, pp. 3143-3147, vol. 7.

Green et al., "Mitochondria and Apoptosis," Science, 1998, pp. 1309-1312, vol. 281.

Grummon et al., Synthesis, Characterization and Crystal Structures of Technetium(V)-Oxo Complexes Useful in Nuclear Medicine. 1. Complexes of Mercaptoacetylglyclglycylglycine ($MAG_3$) and its Methyl Ester Derivative ($MAG_3OMe$), Inorg. Chem., 1995, pp. 1764-1772, vol. 34.

Herr et al., "Activation of CD95 (APO-1/Fas)Signaling by Ceramide Mediates Cancer Therapy-Induced Apoptosis," EMBO J., 1997, pp. 6200-6208, vol. 16.

Hom et al., "Technetium-99m-Labeled Receptor-Specific Small-Molecule Radiopharmaceuticals: Recent Developments and Encouraging Results," Nuclear Med. Biol., 1997, pp. 485-498, vol. 24.

Houghten, "General Method for the Rapid Solid-Phase Synthesis of Large Numbers of Peptides: Specificity of Antigen-Antibody Interaction at the Level of Individual Amino Acids," Proc. Natl. Acad. Sci. USA, 1985, pp. 5131-5135, vol. 85.

Huq et al., "Probing the Proximity of the Core Domain of an HIV-1 Tat Fragment in a Tat-TAR Complex by Affinity Cleaving," Biochem., 1997, pp. 12592-12599, vol. 36.

Jamieson et al., "Structural and Kinetic Studies of a Cisplatin-Modified DNA Icosamer Binding to HMG1 Domain B," J. Biol. Chem., 1999, pp. 12346-12354, vol. 274.

Jayadev et al., "Role for Ceramide in Cell Cycle Arrest," J. Biol. Chem., 1995, pp. 2047-2052, vol. 270.

Jones, "Taking a New TAK on Tat Transactivation," Genes & Dev., 1997, pp. 2593-2599, vol. 11.

Jurisson et al., "Coordination Compounds in Nuclear Medicine," Chemical Rev., 1993, pp. 1137-1156, vol. 93.

Kemp et al., "Protein Kinase Recognition Sequence Motifs," TIBS, 1990, pp. 342-346, vol. 15.

Kennelly et al., "Consensus of Sequences as Substrate Specificity Determinants for Protein Kinases and Protein Phosphatases," J. Biol. Chem., 1991, pp. 15555-15558, vol. 266.

Kubota et al., "Functional Similarity of HIV-1 rev and HTLV-1 rex Proteins: Identification of a New Nucleolar-Targeting Signal in rev Protein," Biochem. Biophys Res. Comm., 1989, pp. 963-970, vol. 162.

Kyte et al., "A Simple Method for Displaying the Hydropathic Character of a Protein," J. Mol. Biol., 1982, pp. 105-132, vol. 157.

Lamson, III et al., "Generator-Produced$^{99m}TcO_4^-$: Carrier Free?" J. Nuclear Medicine, 1975, pp. 639-641, vol. 16.

Li et al., "Synthesis, Metal Chelate Stability Studies, and Enzyme Digestion of a Peptide-Linked Dota Derivative and its Corresponding Radiolabeled Immunoconjugates," Bioconjugate Chemistry, 1993, pp. 275-283, vol. 4.

Li et al., "3-(diethoxyphosphoryloxy)-1,2,3-benzotriazin-4(3H)-one(DEPBT): A New Coupling Reagent with Remarkable Resistance to Racemization," Org. Lett., 1999, pp. 91-94, vol. 1.

Lin et al., "Synthesis of a Biological Active Tumor Growth Factor from the Predicted DNA Sequence of Shope Fibroma Virus," American Chemical Society, 1988, pp. 5640-5645, vol. 27.

Lister-James et al., "Pre-Clinical Evaluation of Technetium-99m Platelet Receptor-Binding Peptide," J. Nuclear Med., 1997, pp. 105-111, vol. 38.

Lister-James et al., "Pharmacokinetic Considerations in the Development of Peptide-Based Imaging Agents," Quarterly Journal of Nuclear Medicine, 1997, pp. 111-118, vol. 41.

Lister-James et al., "Thrombus Imaging with a Technetium-99m-Labeled, Activated Platelet Receptor-Binding Peptide," J. Nuclear Med., 1996, pp. 775-781, vol. 37.

Liu et al., "Labeling Cyclic Glycoprotein IIb/IIIa Receptor Antagonists with $^{99m}Tc$ by the Preformed Chelate Approach: Effects of Chelators on Properties of [$^{99m}Tc$] Chelator-Peptide Conjuates,", Bioconjugate Chem., 1996, pp. 196-202, vol. 7.

Lowry et al., "Protein Measurement with the Folin Phenol Reagent," J. Biol. Chem., 1951, pp. 265-275, vol. 193.

Mann et al., "Endocytosis and Targeting of Exogenous HIV-1 Tat Protein," EMBO J., 1991, pp. 1733-1739, vol. 10.

Meegalla et al., "Synthesis and Characterization of Technetium-99m-Labeled Tropanes as Dopamine Transporter-Imaging Agents," J. Med. Chem., 1997, pp. 9-17, vol. 40.

Merrifield et al., "Synthesis of the Antibacterial Peptide Cecropin A(1033)," American Chemical Society, 1982, pp. 5020-5031, vol. 21.
Nagahara et al., "Transduction of Full-Length TAT Fusion Proteins into Mammalian Cells: TAT-p27$^{Kip1}$ Induces Cell Migration," Nature Med., 1998, pp. 1449-4152, vol. 4.
Nakagawara et al., "High Levels of Expression and Nuclear Localization of Interleukin-1β Converting Enzme (ICE) and CPP32 in Favorable Human Neuroblastomas," Cancer Res., 1997, pp. 4578-4584, vol. 57.
Ogasawara et al., "Lethal Effect of the Anti-Fas Antibody in Mice," Letters to Nature, 1993, pp. 806-809, vol. 364.
Papadopoulos et al., "Correlation of Lipophilicity to Biodistribution of $^{99m}$Tc-Labeled Aminothiols," Nucl. Med. Biol., 1993, pp. 101-104, vol. 20.
Peng et al., "Mitotic and $G_2$, Checkpoint Control: Regulation of 14-3-3 Protein Binding by Phosphorylation of Cdc25C on Serine-216," Science, 1997, pp. 1501-1505, vol. 277.
Peterson et al., "Cathepsin Substrates as Cleavable Peptide Linkers in Bioconjugates, Selected from a Fluorescence Quench Combinatorial Library," Bioconjugate Chemistry, 1998, pp. 618-626, vol. 5.
Piwnica-Worms, "Functional Imaging of Multidrug-Resistant P-Glycoprotein with an Organotechnetium Complex," Cancer Res., 1993, pp. 977-894, vol. 53.
Piwnica-Worms, "Transmembrane Chloride Flux in Tissue-Cultured Chick Heart Cells," J. General Physiology, 1983, pp. 731-748, vol. 81.
Piwnica-Worms et al., "Uptake and Retention of Hexakis (21-Methoxyisobutyl Isonitrile) Technetium (I) in Cultured Chick Myocardial Cells," Circulation, 1990, pp. 1926-1838, vol. 82.
Polyakov et al., "Synthesis and Characterization in vivo of Membrane Permeant Peptide Conjugates for Imaging and Radiotherapy," J Labelled Compounds and Radiopharmaceuticals, 1999, pp. S4-S6, vol. 42 Supp.
Polyakov et al., "Membrane Permeant Peptide Conjugates for Imaging Caspase-3 Activity in vivo," Proceedings of the American Association for Cancer Research Annual Meeting, 1999, p. 729, vol. 40 (Meeting info: 90th Annual Meeting of the American Association for Cancer Research, Philadelphia, PA, 1999, Abstract No. XP002197373).
Polyakov et al., "Characterization of Membrane Permeant Peptide Conjugates for Imaging and Radiotherapy," Book of Abstracts, 217th ACS National Meeting, Anaheim, CA, 1999, Abstract No. XP001073621.
Polyakov et al., "Membrane Permeant Peptide Conjugates for Imaging Apoptosis in vivo," J. Nuclear Medicine, 1999, pp. 78P-79P, vol. 40 (Meeting info: 46th Annual Meeting of the Society of Nuclear Medicine, Los Angeles, CA, 1999, Abstract No. XP002197372).
Polyakov et al., "Novel Tat-Peptide Chelates for Direct Transduction of Technetium-99m and Thenium into Human Cells for Imaging and Radiotherapy," Bioconjugate Chemistry, 2000, pp. 762-771, vol. 11.
Ratner et al., "Complete Nucleotide Sequence of the AIDS Virus, HTLV-III," Nature, 1985, pp. 277-284, vol. 313.
Rogers et al., "Comparison of Four Bifunctional Chelates for Radiolabeling Monoclonal Antibodies with Copper Radioisotopes: Biodistribution and Metabolism," Bioconjugate Chem., 1996, pp. 511-522, vol. 7.
Ruben et al., "Structural and Functional Characterization of Human Immunodeficiency Virus tat Protein," J. Virology, 1989, pp. 1-8, vol. 63.
Silbernagl, "The Renal Handling of Amino Acids and Oligopeptides," Physiological Reviews, 1988, pp. 911-1007, vol. 68.
Talanian et al., "Substrate Specificities of Caspase Family Proteases," J. Biol. Chem., 1997, pp. 9677-9682, vol. 272.
Thornberry et al., "Caspases: Enemies Within," Science, 1998, pp. 1312-1316, vol. 281.
Tokota, "Microautoradiographic Analysis of the Normal Organ Distribution of Radioiodinated Single-Chain Fv and Other Immunoglobulin Forms," Cancer Res., 1993, pp. 3776-3783, vol. 53.
Trimble et al., "Use of Designed Peptide Linkers and Recombinant Hemoglobin Mutants for Drug Delivery: In Vitro Release of an Angiotensin II Analog and Kinetic Modeling of Delivery," Bioconjugate Chem., 1997, pp. 416-423, vol. 8.
Tyagi et al., "Molecular Beacons: Probes that Fluoresce Upon Hybridization," Nature Biotech., 1996, pp. 303-308, vol. 14.
Ubarretxena-Belandia et al., "Outer Membrane Phospholipase A is Dimeric in Phospholipid Bilayers: A Cross-Linking and Fluorescence Resonance Energy Transfer Study," Biochem., 1999, pp. 7398-7405, vol. 38.
Villa et al., "Caspases and Caspase Inhibitors," TIBS, 1997, vol. 22.
Vives et al., "A Truncated HIV-1 Tat Protein Basic Domain Rapidly Translocates Through the Plasma Membrane and Accumulates in the Cell Nucleus," J. Biol. Chem., 1997, pp. 16010-16017, vol. 272.
Vives et al., "Effects of the Tat Basic Domain on Human Immunodeficiency Virus Type 1 Transactivation, Using Chemically Synthesized Tat Protein and Tat Peptides," J. Virology, 1994, pp. 3343-3353, vol. 68.
Waibel et al., "Stable One-Step Technetium-99m Labeling of His-Tagged Recombinant Proteins with a Novel Tc(I)-Carbonyl Complex," Nature Biotechnology, 1999, pp. 897-901, vol. 17.
Welch et al., "A Herpesvirus Maturational Proteinase, Assemblin: Identification of its Gene, Putative Active Site Domain, and Cleavage Site," Proc. Natl. Acad. Sci. USA, 1991, pp. 10792-10796, vol. 88.
Wyllie, "Clues in the p53 Murder Mystery," Nature, 1997, pp. 237-238, vol. 389.
Yaffe et al., "The Structural Basis for 14-3-3: Phosphopeptide Binding Specificity," Cell, 1997, pp. 961-971.
Yuan et al., "The C. Elegans Cell Death Gene ced-3 Encodes a Protein Similar to Mammalian Interleukin-1β-Converting Enzyme," Cell, 1993, pp. 641-652, vol. 75.
Baker et al., "Evaluation of Factors Affecting Mortality Rate After Sepsis in a Murine Cecal Ligation and Puncture Model," Surgery, 1983, pp. 331-335, vol. 94.
Bernal-Mizrachi et al., "Islet β Cell Expression of Constitutively Active Akt1/PKBα Induces Striking Hypertrophy, Hyperplasia, and Hyperinsulinemia," J. Clin. Invest., 2001, pp. 1631-1638, vol. 108.
Chang et al, "Involvement of P13K/Akt Pathway in Cell Cycle Progression, Apoptosis, and Neoplastic Transformation: A Target for Cancer Chemotherapy," Leukemia, 2003, pp. 590-603, vol. 17.
Hiromura et al., "Inhibition of Akt Kinase Activity by a Peptide Spanning the βA Strand of the Proto-Oncogene TCL1," J. Biol. Chem., 2004, pp. 54307-54318, vol. 279.
Hotchkiss et al., "Apoptotic Cell Death in Patients with Sepsis, Shock, and Multiple Organ Dysfunction," Crit. Care Med., 1999, pp. 1230-1251, vol. 27.
Hotchkiss et al., "Caspase Inhibitors Improved Survival in Sepsis: A Critical Role of the Lymphocyte," Nature Immunol., 2000, pp. 496-501, vol. 1.
Li et al., "A Calcium-Sensitive Magnetic Resonance Imaging Contrast Agent," J. Am. Chem. Soc, 1999, pp. 1413-1414, vol. 121.
Song et al., "Antibody Mediated in vivo Delivery of Small Interfering RNAs via Cell-Surface Receptors," Nature Biotech., 2005, pp. 709-717, vol. 23.
Teitell, "The TCL1 Family of Oncoproteins: Co-Activators of Transformation," Nature, 2005, pp. 640-648, vol. 5.
Tuttle et al., "Regulation of Pancreatic β-Cell Growth and Survival by the Serine/Threonine Protein Kinase Akt1/PKBα," Nat. Med., 2001, pp. 1133-1137, vol. 7.

* cited by examiner

Tc-99m-TAT-Casp-3 Conjugate
in Normal FVB Mouse
(30 min post-injection)

Head

— Bladder

Tail

Tc 99m TAT Casp3 Conjugate
in Mouse AntiFas-Induced Apoptosis Model
(30 min post-injection)

(-) AntiFas Ab    (+) AntiFas Ab

MEMBRANE-PERMEANT PEPTIDE COMPLEXES FOR MEDICAL IMAGING, DIAGNOSTICS, AND PHARMACEUTICAL THERAPY

RELATED U.S. PATENT APPLICATIONS

This is a divisional and claims the priority of U.S. application Ser. No. 09/557,465, filed on Apr. 25, 2000 now U.S. Pat. No. 6,589,503, which is incorporated herein by reference as if restated in full. Ser. No. 09/557,465 is a continuation in part of Ser. No. 09/336,093 filed Jun. 18, 1999 and now U.S. Pat. No. 6,348,185 which claims the priority of provisional application Ser. No. 60/090,087 filed Jun. 20, 1998.

BACKGROUND OF THE INVENTION

1. Field of the Invention

The present invention broadly relates to the field of medicine. More specifically, the present invention relates to the fields of medical imaging, diagnostics, and pharmaceutical therapy. The present invention provides methods and compositions for medical imaging, evaluating intracellular processes, radiotherapy of intracellular targets, and drug delivery by the use of novel cell membrane-permeant peptide conjugate coordination and covalent complexes having target cell specificity. The present invention also provides kits for conjugating radionuclides and other metals to the peptide coordination complexes.

2. Description of Related Art

Radiopharmaceuticals in Diagnosis and Therapy

Radiopharmaceuticals provide vital information that aids in the diagnosis and therapy of a variety of medical diseases (Hom and Katzenellenbogen, Nucl. Med. Biol. 24:485-498, 1997). Data on tissue shape, function, and localization within the body are relayed by use of one of the various radionuclides, which can be either free chemical species, such as the gas $^{133}$Xe or the ions $^{123}$I$^{-}$, and $^{201}$Tl$^{-}$, covalently or coordinately bound as part of a larger organic or inorganic moiety, the images being generated by the distribution of radioactive decay of the nuclide. Radionuclides that are most useful for medical imaging include $^{11}$C ($t_{1/2}$ 20.3 min), $^{13}$N ($t_{1/2}$ 9.97 min), $^{15}$O ($t_{1/2}$ 2.03 min), $^{18}$F ($t_{1/2}$ 109.7 min), $^{64}$Cu ($t_{1/2}$ 12 h), $^{68}$Ga ($t_{1/2}$ 68 min) for positron emission tomography (PET) and $^{67}$Ga ($t_{1/2}$ 68 min), $^{99m}$Tc ($t_{1/2}$ 6 h), $^{123}$I ($t_{1/2}$ 13 h) and $^{201}$Tl ($t_{1/2}$ 73.5 h) for single photon emission computed tomography (SPECT) (Hom and Katzenellenbogen, Nucl. Med. Biol. 24:485-498, 1997).

SPECT and PET imaging provide accurate data on radionuclide distribution at the desired target tissue by detection of the gamma photons that result from radionuclide decay. The high degree of spatial resolution of modern commercial SPECT and PET scanners enables images to be generated that map the radionuclide decay events into an image that reflects the distribution of the agent in the body. These images thus contain anatomic and functional information useful in medical diagnosis. Similarly, if the radionuclides decay in such a manner as to deposit radiation energy in or near the target cells or tissues, the same approach would enable therapeutically relevant doses of radioactivity to be deposited within the tissues.

Many radiopharmaceuticals have been prepared whose tissue localizing characteristics depend on their overall size, charge, or physical state (Hom and Katzenellenbogen, Nucl. Med. Biol. 24:485-498, 1997). Other radiopharmaceuticals are synthesized with the intention to be ligands for specific hormone, neurotransmitter, cell surface or drug receptors, as well as specific high affinity transport systems or enzymes. As these receptors and enzymes are known to be involved in the regulation of a wide variety of vital bodily functions, effective imaging agents can be used in the diagnosis or staging of a variety of disease states, in which such receptors are functioning abnormally or are distributed in an abnormal fashion, or in the monitoring of therapy (Hom and Katzenellenbogen, Nucl. Med. Biol. 24:485-498, 1997). Effective therapeutic agents can also be used to deliver pharmacologically active doses of compounds to the same receptors and enzymes.

Recent advances in molecular, structural and computational biology have begun to provide insights in the structure of receptors and enzymes that should be considered in the design of various ligands. Two key issues derived from the structure and distribution of these receptors have a direct impact on the development of new radiopharmaceuticals: 1) the location of a receptor or enzyme activity in the body (i.e., peripheral sites versus brain sites), and 2) its subcellular location (i.e., on the cell surface versus intracellular) will determine whether a radiopharmaceutical injected intravenously will need to traverse zero, one, two or more membrane barriers to reach the target. The structure of the receptor and the nature of its interaction with the ligand will determine the degree to which large ligands or ligands with large substituents may be tolerated (Hom and Katzenellenbogen, Nucl. Med. Biol. 24:485-498, 1997). For example, radiopharmaceuticals which target cell surface receptors will encounter no membrane barriers to reach their target. Natural ligands for these receptors can be large, and often are charged and, consequently, large radiopharmaceuticals are tolerated. Conversely, for a radiopharmaceutical to reach intracellular receptors or enzymes, at least one membrane barrier, the cell plasma membrane, must be traversed, and if the target site is within the central nervous system, the radiopharmaceutical must also traverse the plasma membranes of endothelial cells of the brain which constitute the blood-brain barrier. Such a situation usually favors radiopharmaceutical designs that strongly minimize ligand size and molecular weight (Hom and Katzenellenbogen, Nucl. Med. Biol. 24:485-498, 1997). Thus, as the number of membrane barriers increases, a premium is placed on keeping the size of a conventional radiopharmaceutical small (<600 Da) and the lipophilicity intermediate (characterized by an octanol-water partition coefficient, log P~2) to enable the agent to traverse membranes (Dishino, et al., J Nucl Med 24: 1030-1038, 1983; Papadopoulos, et al., Nucl Med Biol 20:101-104, 1993; Eckelman, Eur J Nucl Med 22:249-263, 1995). This has conventionally precluded the use of peptide radiopharmaceuticals for intracellular targets.

There has been a great deal of research into the development of radiopharmaceuticals directed toward cell surface receptors whose natural ligands are peptides. Tc-labeled peptides can span the spectrum of size. The derivatizing group or chelation core of smaller peptides has been reported to impact the in vitro binding and in vivo distribution properties of these compounds (Babich and Fischman, Nucl Med Biol 22:25-30, 1995; Liu, et al., Bioconj Chem 7:196-202, 1996). For larger peptides or proteins, the labeling process can usually occur at one or more of several reactive sites, and thus, the final mixture of compounds is less chemically defined. Thus, for larger proteins, it is usually much less clear which of these sites, if any, might be more favorable for receptor interaction and whether or not specific labeling would increase biological activity of the agent (Hom and Katzenellenbogen, *Nucl. Med. Biol.* 24:485-498, 1997).

It is known that low molecular weight peptides and antibody fragments provide rapid tumor targeting and uniform distribution in tumor tissues (Yokota et al., *Cancer Res* 53:3776-3783, 1993). While such characteristics render low molecular weight peptides attractive vehicles for the delivery of radioactivity to tumor tissues and organs for both targeted imaging and radiotherapy, nonetheless problems have been encountered. High and persistent localization of the radioactivity is observed in the kidneys, which compromises tumor visualization in the kidney region and limits therapeutic potential (Buijs, et al., *J Nucl Med* 33:1113-1120, 1992; Baum, et al., *Cancer* (Phila) 73:896-899, 1994; Choi, et al., *Cancer Res* 55:5323-5329, 1995; Behr, et al., *J Nucl Med* 36:430-441, 1995). As discussed by Arano, et al. (*Cancer Res* 59:128-143, 1999), radiolabeled low molecular weight peptides and antibody fragments would become much more useful for targeted imaging and therapy if the renal radioactivity levels could be reduced without impairing those in the target tissue. Previous studies have indicated that radiolabeled low molecular weight peptides and antibody fragments are likely resorbed by proximal tubules via luminal endocytosis after glomerular filtration (Silberbagl, S. *Physiol Rev* 68:811-1007, 1988). The long residence times of the radiometabolites generated after lysosomal proteolysis of the radio labeled fragments in renal cells were also reported to be responsible for the persistent renal radioactivity levels (Choi, et al., *Cancer Res* 55:5323-5329; Rogers, et al., *Bioconjugate Chem* 7:511-522, 1996).

There exists a continued need for peptide-based radiopharmaceuticals that are rapidly cleared and target intracellular receptors or enzyme activities.

Peptide-Based Metal Coordination Complexes

Small peptides can be readily prepared by automated solid phase peptide synthesis (Merifield et al., *Biochemistry* 21:5020-5031, 1982; Houghten, *Proc Natl Acad Sci USA* 82:5131-5135, 1985; Lin, et al., *Biochemistry* 27:5640-5645, 1988) using anyone of a number of well known, commercially available automated synthesizers, such as Applied Biosystems ABI 433A peptide synthesizer. Many combinations of natural and non-natural amino acids and peptide sequence mimetics (peptidomimetics) are possible, and selective engineering of favorable target-binding and pharmacokinetic properties can be accomplished with natural and unnatural peptides (Lister-James et al., *Q. J: Nucl. Med.,* 41:111-118, 1997). Peptidomimetics are unnatural biopolymers that do not contain α-amino acids, but rather incorporate backbone structures with hydrogen-bonding groups (such as urea), chiral centers, side chain functionalities, and a sufficient degree of conformational restriction to behave similar to, or mimic the bioactivities of, a natural polypeptide. Peptide-based imaging agents are also well known (Lister-James et al., *Q. J: Nucl. Med.,* 41:111-118, 1997; Lister-James et al., *J. Nucl. Med.,* 38:105-111, 1997), especially those that incorporate Tc-99m as the radionuclide, the most commonly used isotope in medical imaging.

The metallic character of Tc-99m requires that it be stabilized by a chelation system to be coupled to an imaging agent. This chelator may typically involve a multiple heteroatom coordination system, or the formation of a non-labile organometallic species. There are two broad strategies for binding metals for biological applications. These are "the pendant approach" and "the integrated approach," which have been recently reviewed by Katzenellenbogen and colleagues (Horn and Katzenellenbogen, *Nucl. Med. Biol.,* 24:485-498, 1997). The pendant (or conjugate) approach involves the strategic placement of a Tc-99m-chelator-tether moiety at a site on the ligand that will not hinder binding of the ligand to its high affinity receptor. The integrated approach replaces a component of a known high-affinity receptor ligand with the requisite Tc-99m chelator such that there is a minimal change in the size, shape, structure, and binding affinity of the resultant molecule. Applications involving peptide-based imaging agents typically use the conjugate design, whereby an appropriate metal chelating moiety is affixed to the amino or carboxy terminus of the targeting peptide.

A variety of metal chelation systems have been developed for synthesis of radioisotopic and magnetic resonance peptide-based imaging agents. Peptide-based agents target extracellular or externally oriented membrane bound receptors (Hom and Katzenellenbogen, *Nucl. Med. Biol.,* 24:485-498, 1997) because the charge, size, and pharmacokinetic properties of typical peptide structures do not allow diffusion across the lipid bilayer of the cell plasma membrane. This limitation has prevented peptide metal chelates from reporting the functional status or biological activity of intracellular receptors or enzymes or other homeostatic activities and intracellular targets. Although techniques and reagents for labeling antibodies and antibody fragments with metal-chelates are well known in the art (Hom and Katzenellenbogen, *Nucl. Med. Biol.,* 24:485-498, 1997, and references therein), they target extracellular or externally oriented cell surface receptors.

Tat Proteins and Peptides

Tat is an 86-amino acid protein involved in the replication of human immunodeficiency virus type 1 (HIV-1). The HIV-1 Tat transactivation protein is efficiently taken up by cells (Mann and Frankel, *EMBO,* 10:1733-1739, 1991; Vives et al., *J. Virol.,* 68:3343-3353, 1994), and low concentrations (nM) are sufficient to transactivate a reporter gene expressed from the HIV-1 promoter (Mann and Frankel, *EMBO,* 10:1733-1739, 1991). Exogenous Tat protein is able to translocate through the plasma membrane and reach the nucleus to transactivate the viral genome (Frankel and Pabo, *Cell* 55:1189-1193, 1988; Ruben, et al, *J Virol* 63:1-8, 1989; Garcia, et al., *EMBO J* 7:3143, 1988; Jones, *Genes Dev* 11:2593-2599, 1997).

A region of the Tat protein centered on a cluster of basic amino acids is responsible for this translocation activity (Vives et al., *J Biol. Chem.,* 272:16010-16017, 1997). Tat peptide-mediated cellular uptake and nuclear translocation have been demonstrated in several systems (Vives, et al., *J Biol Chem* 272:16010-16017, 1997; Jones, *Genes Dev* 11:2593-2599, 1997). Chemically coupling a Tat-derived peptide (residues 37-72) to several proteins results in their internalization in several cell lines or tissues (Fawell, et at, *Proc Natl Acad Sci USA* 91:664-668, 1994; Anderson, et at, *Biochem Biophys Res Commun* 194:876-8884, 1993; Fahraeus, et al., *Curr Biol* 6:84-91, 1996; Nagahara, et al, *Nat Med* 4:1449-1452, 1998). A synthetic peptide consisting of the Tat basic amino acids 48-60 with a cysteine residue at the C-terminus coupled to fluorescein maleimide translocates to the cell nucleus as determined by fluorescence microscopy (Vives et al., *J. Biol. Chem.,* 272:16010-16017, 1997). In addition, a fusion protein (Tat-NLS-β-Gal) consisting of Tat amino acids 48-59 fused by their amino-terminus to β-galactosidase amino acids 9-1023 translocates to the cell nucleus in an ATP-dependent, cytosolic factor-independent manner (Efthymiadis et al., *J. Biol. Chem.*, 273:1623-1628, 1998).

While the literature teaches that Tat peptide constructs and similar membrane permeant peptides readily translocate into the cytosolic and nuclear compartments of living cells, little is known regarding the cellular retention characteristics over time once the permeant peptide constructs are no longer in contact with the cell surface from the extracellular fluid spaces. Furthermore, no information is available regarding the pharmacokinetic and distribution characteristics of membrane-permeant peptides within a whole living organism, animal or human.

Apoptosis

Chemotherapeutic drugs used in the treatment of cancer are thought to interact with diverse cellular targets in conferring lethal effects on mammalian cells. Recently, anticancer agents, irrespective of their intracellular target, have been shown to exert their biological effect in target cells by triggering a common final death pathway known as apoptosis (Fulda, et al., *Cancer Res* 57:3823-3829, 1997; Fisher, *Cell* 78:539-542, 1994). Thus, there exists mounting evidence that many anticancer treatments may kill through apoptosis by activating intracellular death machinery in the target cell rather than by simply crippling various components of cellular metabolism (Fulda, et al., *Cancer Res* 57:3823-3829, 1997; Fisher, *Cell* 78:539-542, 1994). In fact, the action of ionizing radiation, drug therapy, and withdrawal of physiological survival factors all appear to act as death stimuli in promoting execution of this common apoptotic pathway (Evan and Littlewood, *Science* 281:1317-1322, 1998; Ashkenazi and Dixit, *Science* 281:1305-1308, 1998). Thus, new models of resistance to therapy have begun to focus on mechanisms that antagonize execution of the apoptotic pathway.

Apoptotic stimuli can arise from the nucleus, cell membrane surface, or the mitochondria (Wyllie, *Nature*, 389: 237-38, 1997). Ultimately, the stimuli converge on a process of activation of a family of interleukin 1β-converting enzymes {(ICE)-like cysteine proteases} known as cysteine aspartases ("caspases") (Thornberry et al., *Science,* 281: 1312-16, 1998). Members of the caspase family are activated in apoptosis and have been shown to be necessary for programmed cell death in a number of biological systems (Yuan et al., *Cell,* 75:641-52, 1993; Thornberry et al., *Science,* 281:1312-16, 1998). The caspase gene family, defined by sequence homology, is also characterized by conservation of key catalytic and substrate-recognition amino acids (Talanian et al., *J. Biol. Chem.,* 272:9677-82, 1997). Thirteen mammalian caspases (1 through 13) have thus far been isolated, having distinct roles in apoptosis and inflammation (Thornberry et al., *Science,* 281:1312-16, 1998). In apoptosis, some caspases are involved in upstream regulatory events and are known as "initiators," while others are directly responsible for proteolytic cleavages that lead to cell disassembly and are known as "effectors." Evidence indicates that caspases transduce or amplify signals by mutual activation. For example, Fas-induced apoptosis is characterized by an early, transient caspase-1-like protease activity followed by a caspase-3-like activity, suggesting an ordered activation cascade (Enari et al., *Nature,* 380:723-26, 1996). Other data suggest that both caspase-3 and caspase-7 are activated by caspase-6 and caspase-10 (Thornberry et al., *Science,* 281:1312-16, 199; Fernandes-Alnemri, *Proc. Natl. Acad. Sci. USA,* 93:7464-69, 1996). Thus, while the activation cascade hypothesis remains to be absolutely proven (Villa et al., *Trends in Biochem. Sci.,* 22:388-93, 1997), circumstantial evidence strongly points to caspase-3 as one key "effector" caspase, standing at the center of the execution pathway of the cell death program.

Caspases are some of the most specific of the proteases, showing an absolute requirement for cleavage after aspartic acid (Thornberry et al., *Science,* 281:1312-16, 1998). Recognition of at least four amino acids, amino terminal to the cleavage site, is also necessary for efficient catalysis. The preferred recognition motif differs significantly between caspases, thereby contributing to their biologically diverse functions (Talanina et al., *J. Biol. Chem.* 272:9677-82, 1997). In addition to high specificity, caspases are also highly efficient, with $K_{cat}/K_m$ values$>10^6$ $M^{-1}s^{-1}$ (Thornberry et al., *Science,* 281:1312-16, 1998). When viewed from the perspective of a molecular target for oncological imaging, this is a key property of the caspases that allows detection of caspase activity in vivo by radiosubstrates. Another advantage of the caspases as imaging targets centers on the nature of the biochemical reaction. Because normal cells have essentially non-detectable levels of caspase activity, and once activated, the "caspase cascade" amplifies reaction rates to maximal velocities (Thornberry et al., *Science,* 281:1312-16, 1998), the signal readout obtained by imaging is binary in character. That is, in the absence of caspase activity, the imaging signal will be low, and when activated, a highly amplified imaging signal will result. This renders the caspase-mediated enzymatic reaction essentially zero-order in situ and, therefore, independent of radiotracer concentration or specific activity, thus eliminating the complexities of first or higher order reaction rates.

Deregulation of apoptosis resulting in insufficient cell death can occur in cancer, allowing malignant tissues to grow (Thornberry et al., *Science,* 281:1312-16, 1998). Conversely, some diseases involve excess apoptosis, such as neurodegenerative disease, ischemia-reperfusion, graft-vs-host disease, and autoimmune disorders (Thornberry et al., *Science,* 281: 1312-16, 1998). Accordingly, two-fold strategies for therapeutic intervention are actively underway within the pharmaceutical industry, one to selectively induce apoptosis through caspase activation, the other to inhibit caspase activity. In order to assess the treatments to alter apoptosis, an accurate means to assess apoptoic activity in vivo is needed.

Inactive pro-caspases are constitutively expressed as proenzymes in nearly all cells, existing in latent forms in the cell cytoplasm (Villa et al., *Trends in Biochem. Sci.* 22:388-93, 1997). Thus, while caspase-3 can be readily identified by Western blots, this requires biopsy material and lysis of the cells. Furthermore, activation of caspase-3 is only inferred by observation of lower molecular weight cleavage fragments on the blot. Activation of caspase-3 has also been inferred from nuclear shifts of antigen by immunohistochemical analysis of biopsy material and shown to be associated with a more favorable prognosis in, for example, pediatric neuroblastoma (Nakagawara et al., *Cancer Res.* 57:4578-84, 1997). However, these indirect methods only imply activation. Thus, the simple determination of the presence or absence of caspase proteins is not necessarily diagnostically useful. A method to directly and non-invasively detect and quantify the enzymatic activity of caspases in order to monitor the commitment to cell death pathway is needed. Because caspases are cytosolic enzymes, new diagnostic and therapeutic compounds are required that can readily cross cell membranes, and whose specificity is based on the presence of protease activity.

Tat Peptide Complexes

Frankel et al. (U.S. Pat. Nos. 5,804,604; 5,747,641; 5,674,980; 5,670,617; 5,652,122) discloses the use of Tat peptides to transport covalently linked biologically active cargo molecules into the cytoplasm and nuclei of cells. Frankel only discloses covalently linked cargo moieties, and does not teach or suggest the attachment of metals to Tat peptides by metal coordination complexes. Specifically, Frankel does not teach the use of peptide chelators to introduce radioimaging materials into cells. In addition, while Frankel teaches the use of cleavable coupling reagents between the Tat protein and the cargo molecule, the cleavable linkers disclosed are non-specific, such that the retention of the cargo molecule is not limited to specific cells.

Anderson et al. (U.S. Pat. Nos. 5,135,736 and 5,169,933) discloses the use of covalently linked complexes (CLCs) to introduce molecules into cells. CLCs comprise a targeting protein, preferably an antibody, a cytotoxic agent, and an enhancing moiety. Specificity is imparted to the CLC by means of the targeting protein, which binds to the surface of the target cell. After binding, the CLC is taken into the cell by endocytosis and released from the endosome into the cytoplasm. In one embodiment, Anderson discloses the use of the Tat protein as part of the enhancing moiety to promote translocation of the CLC from the endosome to the cytoplasm. In another embodiment, Anderson discloses the use of CLCs to transport radionuclides useful for imaging into cells. The complexes described by Anderson are limited in their specificity to cells that can be identified by cell surface markers. Many biologically and medically significant cellular processes, for example caspase protease activities discussed above, are not detectable with cell surface markers. In addition, the attachment of enhancing moieties to the CLC is accomplished by the use of bifunctional linkers. The use of bifunctional linkers results in the production of a heterogeneous population of CLCs with varying numbers of enhancing moieties attached at varying locations. This can lead to the production of CLCs in which the biological activity of the targeting protein, the enhancing moiety, or both, are lost. Another disadvantage of CLCs is that the number and location of linked enhancing moieties will vary with each reaction, so that a consistent product is not produced.

There is a need in the art for cell membrane-permeant peptide complexes of uniform composition, capable of delivering radionuclides, other metals, diagnostic substances such as fluorochromes, dyes, etc., and therapeutic and cytotoxic drugs into cells in a specific and selective manner. Furthermore, rapid clearance of the complexes from non-target cells and tissues of the body would facilitate and enhance the utility of such complexes in vivo.

SUMMARY OF THE INVENTION

The present inventor has surprisingly discovered that the addition of D-amino acid containing membrane-permeant peptides attached to non- or poorly permeant drugs, diagnostic and/or therapeutic substances such as oligonucleotides, peptides, peptide nucleic acids, fluorochromes, dyes, enzyme substrates, and metals useful in medical therapy, imaging, and/or diagnostics greatly increases their accumulation within cells. As shown in Example 14, this increase in accumulation is on the order of 8- to 9-fold as compared to membrane-permeant peptides comprising only naturally occurring L-amino acids. Thus, use of the D-amino acid containing membrane-permeant peptides of the present invention allows delivery of greater amounts of therapeutic or diagnostic substances to the interior of cells either in vivo or in vitro than was heretofore possible using membrane permeant peptides containing only L-amino acids.

The present inventor has also discovered that the Tat peptide and other cell membrane-permeant peptides can be used to selectively deliver non- or poorly permeant drugs, diagnostic and/or therapeutic substances such as oligonucleotides, peptides, peptide nucleic acids, fluorochromes, dyes, enzyme substrates, and metals useful in medical therapy, imaging, and/or diagnostics selectively to cells in vivo only when functional linkers are introduced into the permeant peptide construct, and has developed methods for linking these substances to Tat and other peptides for use in such methods. As illustrated in Examples 6 and 10, below, non-targeted Tat peptides, rather than being trapped inside cells and tissues indefinitely, are cleared surprisingly rapidly from body tissues when introduced into the living organism. Furthermore, non-functionalized prototypes of such complexes are rapidly excreted by the kidneys and cleared from the whole body. Thus, membrane-permeant peptides covalently linked to oligopeptides, proteins, oligonucleotides, and drugs as known previously possess rapid and ineffective biological half-times within the whole organism.

Thus, in response to this surprising and unanticipated property of D-amino acid containing permeant peptides and to improve upon the prior art, the present invention provides novel permeant peptide conjugates, complexes and methods that possess the advantage of enabling the targeted trapping of greater amounts of such compounds or fragments thereof within desired cells, tissues and organs of the intact body of living organisms. Conversely, when it is desired to increase the rates of clearance of cargo oligopeptides, proteins, oligonucleotides, metals, and drugs, the present invention also provides methods that will enhance their rates of clearance from the body.

Accordingly, in a first aspect, the present invention provides a compound comprising a cell membrane-permeant peptide; a diagnostic or pharmaceutically active substance; and a functional linker moiety linking the peptide and the diagnostic or pharmaceutically active substance, wherein the compound further comprises at least one D-amino acid and the functional linker moiety confers target cell specificity to the compound, or a pharmaceutically acceptable salt of the compound.

In a second aspect, the present invention provides a composition comprising, a compound comprising a cell membrane-permeant peptide; a diagnostic or pharmaceutically active substance; and a functional linker moiety linking the peptide and the diagnostic or pharmaceutically active substance, wherein the compound further comprises at least one D-amino acid and the functional linker moiety confers target cell specificity to the compound. The composition can further comprise a pharmaceutically acceptable carrier, excipient, or diluent.

In a third aspect, the present invention provides a kit comprising, a compound comprising a cell membrane-permeant peptide; a metal chelation ligand; and a functional linker moiety linking the peptide and the metal chelation ligand, wherein the compound further comprises at least one D-amino acid and the functional linker moiety confers target cell specificity to the compound, and a reducing agent capable of reducing a metal that can be coordinately incorporated into the metal chelation ligand.

In another aspect, the present invention provides a method for imaging cells in vivo, comprising administering to an animal a cell imaging effective amount of a compound comprising a cell membrane-permeant peptide; a chelated radionuclide or a chelated relaxivity metal; and a functional linker moiety linking the peptide and the chelated radionuclide or the chelated relaxivity metal, the functional linker confering target cell specificity to the compound, and monitoring or evaluating the location of the radionuclide or relaxivity metal within the animal. Further the compound may comprise at least one D-amino acid.

In another aspect, the present invention provides a method for imaging cells in vitro, comprising contacting the cells with a cell imaging effective amount of a compound comprising a cell membrane-permeant peptide; a diagnostic substance; and a functional linker moiety linking the peptide and the diagnostic substance, wherein the functional linker confers target cell specificity to the compound, and monitoring or evaluating the presence of the diagnostic substance within the cells. Further, the compound may comprise at least one D-amino acid.

In a further aspect, the present invention provides a method for detecting cellular apoptosis in vivo, comprising administering to an animal a cellular apoptosis detecting effective amount of a compound comprising a cell membrane-permeant peptide; a diagnostic substance; and a functional linker moiety linking the peptide and the diagnostic substance, wherein the functional linker moiety comprises a caspase-reactive sequence, and monitoring the diagnostic substance within the animal. Further, the compound may contain at least one D-amino acid.

In another aspect, the present invention provides a method for detecting cellular apoptosis in vitro, comprising contacting cells or tissue in vitro with a cellular apoptosis detecting effective amount of a compound comprising a cell membrane-permeant peptide; a diagnostic substance; and a functional linker moiety linking the peptide and the diagnostic substance, wherein the functional linker moiety comprises a caspase-reactive sequence, and monitoring the diagnostic substance within the cells or tissue. Further, the compound may contain at least one D-amino acid.

In yet another aspect, the present invention provides a method for detecting an enzyme in a cell, comprising contacting the cell with an enzyme detecting effective amount of a compound comprising a cell membrane-permeant peptide; a diagnostic substance; a functional linker moiety linking the peptide and the diagnostic substance, wherein the functional linker moiety comprises a sequence reactive with the enzyme; removing unreacted compound from the locus of the cell so that the signal to noise ratio is sufficient for diagnostic purposes; and monitoring the presence of the diagnostic substance in the cell. Such monitoring can be performed quantitatively, and the cell can be present within a living animal. Furthermore, the enzyme can be one that is characteristically associated with a disease, condition, or disorder. Further, the compound may contain at least one D-amino acid.

In yet another aspect, the present invention provides a method for diagnosing the presence of a disease, condition, or disorder in an animal, comprising administering to the animal a diagnostically effective amount of a compound comprising a cell membrane-permeant peptide; a diagnostic substance; a functional linker moiety linking the peptide and the diagnostic substance, wherein the functional linker moiety confers target cell specificity to the compound, and which comprises a sequence reactive with an enzyme indicative or characteristic of the disease, condition, or disorder, and monitoring the diagnostic substance within the animal. By way of example, the disease, condition, or disorder can be a cancer such as a central nervous system tumor, breast cancer, liver cancer, lung cancer, head cancer, neck cancer, a lymphoma, or a melanoma. Further, the compound may contain at least one D-amino acid.

In still another aspect, the present invention provides a method of assessing the effectiveness of cancer therapy, comprising administering to an animal undergoing cancer therapy a diagnostically effective amount of a compound comprising a cell membrane-permeant peptide; a diagnostic substance; and a functional linker moiety linking the peptide and the diagnostic substance, wherein the functional linker moiety confers target cell specificity to the compound, and which comprises a caspase-reactive sequence, and monitoring the diagnostic substance within the animal. Such monitoring can be performed quantitatively. Furthermore, the method can be repeated at intervals during the cancer therapy, and the quantity of the diagnostic substance detected within the animal at each interval can be compared to the quantity of the diagnostic substance detected at previous intervals to determine the effectiveness of the therapy. In addition, the compound may contain at least one D-amino acid.

In yet another aspect, the present invention provides a method of delivering a pharmaceutically active substance to a cell, comprising contacting the cell with an effective amount of a compound comprising a cell membrane-permeant peptide; a pharmaceutically active substance; and a functional linker moiety linking the peptide and the pharmaceutically active substance, wherein the compound further comprises at least one D-amino acid and the functional linker moiety confers target cell specificity to the compound.

In another aspect, the present invention provides a method of treating, inhibiting, or preventing a disease, condition, or disorder responsive to treatment with a pharmaceutically active substance in an animal, comprising administering to the animal a pharmaceutically effective amount of a compound comprising a cell membrane-permeant peptide; a pharmaceutically active substance; and a functional linker moiety linking the peptide and the pharmaceutically active substance, wherein the compound further comprises at least one D-amino acid and the functional linker moiety confers target cell specificity to the compound.

In another aspect, the present invention provides a method for selectively destroying cells expressing a selected enzyme activity, comprising contacting the cells with a cell-destroying effective amount of a compound comprising a cell membrane-permeant peptide; a cytotoxic substance; and a functional linker moiety linking the peptide and the cytotoxic substance, wherein the compound further comprises at least one D-amino acid and the functional linker moiety confers target cell specificity to the compound.

In yet another aspect, the present invention provides a method for assessing the effect of a drug in altering the expression or activity of an enzyme in a target cell, comprising contacting the target cell with a diagnostically effective amount of a compound comprising a cell membrane-permeant peptide; a diagnostic substance; a functional linker moiety linking the peptide and the diagnostic substance, wherein the functional linker moiety confers target cell specificity to the compound, and which comprises a sequence capable of interacting with the enzyme so as to release the diagnostic substance from the compound into the interior of the cell; clearing unreacted compound from the locus of the cell so that the signal to noise ratio is sufficient for diagnostic purposes; and monitoring or evaluating the diagnostic substance in the target cell. Such monitoring can be performed quantitatively, and the target cell can be present within a living animal. Furthermore, the enzyme can be associated with a disease, condition, or disorder. In addition, the compound may further comprise at least one D-amino acid.

In yet another aspect, the present invention provides a method for detecting the expression of a nucleic acid sequence, which can be DNA or RNA, encoding an enzyme, a receptor, or a binding protein introduced into a cell, comprising contacting the cell with a compound comprising a cell membrane-permeant peptide; a diagnostic substance; a functional linker moiety linking the peptide and the diagnostic substance, wherein the functional linker moiety confers target cell specificity to the compound, and which comprises a sequence capable of interacting with the enzyme, receptor, or binding protein so as to selectively retain the diagnostic substance in the cell, and monitoring the diagnostic substance in the cell. Further, the compound may comprise at least one D-amino acid.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

The following detailed description is provided to aid those skilled in the art in practicing the present invention. Even so, this detailed description should not be construed to unduly limit the present invention as modifications and variations in the the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

As used herein, the term "animal" includes, but is not limited to, mammals, including human beings. It should be noted that the complexes and methods disclosed herein are applicable in both human and veterinary medicine. Thus, the present compounds and methods can be applied to humans, domestic pets such as cats, dogs, rodents, birds etc., farm animals such as cows, sheep, goats, pigs, horses, etc., zoo animals, etc.

Amino acids are indicated herein using the single letter notation conventional in the art. When used in amino acid sequences, the letter "x" designates any amino acid. When used in an amino acid sequence, a "/" between two adjacent letters indicates that either of the amino acids listed can be used. When used in nucleotide sequences, the letter "n" designates A, T, C or G.

Structure of Membrane-Permeant Peptide Covalent and Coordination Complexes

Figure 1:
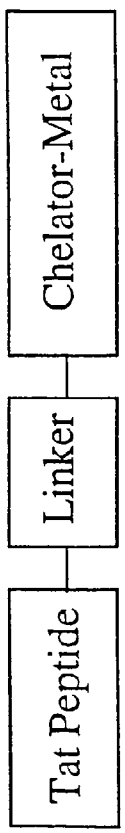
FIG. 1 shows the general structure of a cell membrane-permeant peptide coordination complex of the present invention.

The general structure of the present invention compounds comprises a unique combination of peptide components to produce a new class of imaging and therapeutic conjugates that will enable interrogation of, and/or interaction with, the desired intracellular processes within living cells in the whole organism. This novel class of agents in its simplest form comprises three components: 1) a cell membrane-permeant peptide sequence made up of D-amino acids, L-amino acids or a combination of D- and L-amino acids; 2) a functional or non-functional linker motif; and 3) a chelator moiety able to coordinate metals useful in medical imaging and therapy (FIG. 1), or other cargo molecule such as a diagnostic substance or pharmaceutically active agent. The HIV-1 Tat basic peptide sequence is an example of the prototypic cell membrane-permeant component. The linker region can comprise amino acid residues, or substituted or unsubstituted hydrocarbon chains useful for connecting the Tat peptide and the metal chelator, for example, via peptide bonds. The linker region can be designed to be non-functional or functional. "Non-functional" refers to non-reactive hydrocarbon chains, simple amino acid sequences, or other sequences that simply bind covalently to the Tat peptide residues on one end and the cargo molecule on the other end. A "functional linker" can comprise amino acid residues that confer biological properties useful for imaging, diagnostics, therapy, etc. Such a functionality could include peptide or protein binding motifs, protein kinase consensus sequences, protein phosphatase consensus sequences, or protease-reactive or protease-specific sequences. Protease sequences are particularly useful as they will result in amplification of an imaging, radiotherapeutic, diagnostic, or therapeutic effect through enzymatic action on the conjugate complex, thereby increasing the intracellular concentration of a cleaved and subsequently trapped metal-chelate or other cargo molecule.

Cell Membrane-Permeant Peptides

The cell membrane-permeant basic peptide component of the complexes of the present invention can comprise any amino acid sequence that confers the desired intracellular translocation and targeting properties to the covalent or coordination complexes. Preferably, these amino acid sequences are characterized by their ability to confer transmembrane translocation and internalization of a complex construct when administered to the external surface of an intact cell, tissue or organ. The complex would be localized within cytoplasmic and/or nuclear compartments as demonstrated by a variety of detection methods such as, for example, fluorescence microscopy, confocal microscopy, electron microscopy, autoradiography, or immunohistochemistry.

Cell membrane-permeant peptide sequences useful in practicing the present invention include, but are not limited to, RQARRNRRRRWRERQR-51 (HIV-1 Rev protein basic motif; SEQ ID NO: 1); MPKTRRRPRRSQRKRPPTP-119 (HTLV-1 Rex protein basic motif; SEQ ID NO: 2) (Kubota et al., *Biochem. Biophys. Res. Comm.*, 162:963-970, 1989); the third helix of the homeodomain of *Antennapedia* (Derossi, et al., *J. Biol. Chem.* 271:18188-93, 1996) (43-RQILIWFQNRRMKWLL-58 (SEQ ID NO: 3)); a peptide derivable from the heavy chain variable region of an anti-DNA monoclonal antibody (Avrameas, et al., *Proc. Natl. Acad. Sci.* 95:5601-06, 1998) (VAYISRGGVSTYYS-DTVKGRFTRQKYNKRA (SEQ ID NO: 4)); and the Herpes simplex virus YP22 protein (Elliot and O'Hare, *Cell*, 88:223-33, 1997) (1-MTSRRSVKSGPREVPRDEYED-LYYTPSSGMASPDSPPDTSRRGALQTRSRQRG EVR-FVQYDESDYALYGGSSSEDDEHPE-VPRTRRPVSGAVLSGPGPARAPPPPA GSGGAGRTPTTAPRAPRTQRVATKAPAA-PAAETTRGRKSAQPESAALPDAPA SRAPTVQLWQM-SRPRTDEDLNELGITHRVTVCEGKNLLQ-RANELVNPDVV QDVDAATATRGRSAASRPTERPRAPAR-SASRPRRPVE-246 (SEQ ID NO: 5)). In a preferred embodiment, the basic peptide is derivable from the human immunodeficiency virus type 1 (HIV-1) Tat protein (Fawell et al., *Proc. Natl. Acad. Sci.*, 91:664-68, 1994). In particular, the Tat peptide can comprise any sequential residues of the Tat protein basic peptide motif 37-72 (Vives et al., *J. Biol. Chem.*, 272:16010-16017, 1997) (37-CFITKALGI-SYGRKKRRQRRRPPQGSQTHQVSLSKQ-72 (SEQ ID NO: 6). The minimum number of amino acid residues can be in the range of from about three to about nine, preferably from about three to about five, and most preferably about four, i.e., the minimal requirement for one alpha helical turn. A preferred embodiment comprises Tat protein residues 48-57 (GRKKRRQRRR) (SEQ ID NO: 7). In one preferred embodiment any of the aforementioned membrane peptides may contain at least one D-amino acid. In another preferred embodiment, a majority of the amino acid residues in any of the aforementioned peptides can comprise D-amino acids. In yet another preferred embodiment, any of the aforementioned peptides are comprised entirely of D-amino acids in forward sequence or inverse sequence (retro-inverse).

As used herein, the term "amino acid" is applicable not only to cell membrane-permeant peptides, but also to linker moieties, coordination ligands, and other cargos, including pharmaceutical agents, i.e., all the individual components of the present complexes. The term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, β-alanine, ornithine, etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

The incorporation of non-natural amino acids, including synthetic non-native amino acids, substituted amino acids, or one or more D-amino acids into the peptides (or other components of the complexes) of the present invention (subsequently referred to herein as "D-peptides") is advantageous in a number of different ways. D-amino acid-containing peptides exhibit increased stability in vitro or in vivo compared to L-amino acid-containing counterparts. Thus, the construction of peptides incorporating D-amino acids can be particularly useful when greater intracellular stability is desired or required. More specifically, D-peptides are resistant to endogenous peptidases and proteases, thereby providing better oral transepithelial and transdermal delivery of linked drugs and conjugates, improved bioavailability of membrane-permeant complexes, and prolonged intravascular and interstitial lifetimes when such properties are desirable. The use of D-peptides can also enhance transdermal and oral transepithelial delivery of linked drugs and other cargo molecules. As shown in Example 14, the use of D-amino acids in the membrane permeant peptide greatly increases the accumulation of linked drugs or other cargo molecules into cells. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-peptide membrane permeant sequences, L-peptide functional linker domains, and D-peptide chelation sequences. In this embodiment, only the functional L-peptide linker region would be able to interact with native enzymatic activities such as proteases, kinases, and phosphatases, thereby providing enhanced selectivity, prolonged biological half-life, and improved signal-to-noise ratio for selected imaging applications. On the other hand, when it is more desirable to allow the peptide to remain active for only a short period of time, the use of L-amino acids in the peptide can allow endogenous peptidases in a cell to digest the peptide in vivo, thereby limiting the cell's exposure to the membrane-permeant peptide covalent and coordination complexes comprising the peptides disclosed herein. It will be apparent that it is possible to construct complexes in which different portions contain either D- or L-amino acids. For example and without limitation, it is possible to construct a complex in which a cell permeant peptide and a metal chelator comprised of D-amino acids are connected by a functional linker comprised of L-amino acids. Other such combinations will be readily apparent to those of ordinary skill in the art and are within the scope of the present invention.

In addition to using D-amino acids, those of ordinary skill in the art are aware that modifications in the amino acid sequence of a peptide, polypeptide, or protein can result in equivalent, or possibly improved, second generation peptides, etc., that display equivalent or superior functional characteristics when compared to the original amino acid sequence. The present invention accordingly encompasses such modified amino acid sequences. Alterations can include amino acid insertions, deletions, substitutions, truncations, fusions, inversions, shuffling of subunit sequences, and the like, provided that the peptide sequences produced by such modifications have substantially the same functional properties as the naturally occurring counterpart sequences disclosed herein. Thus, for example, modified cell membrane-permeant peptides should possess substantially the same transmembrane translocation and internalization properties as the naturally occurring counterpart sequence.

One factor that can be considered in making such changes is the hydropathic index of amino acids. The importance of the hydropathic amino acid index in conferring interactive biological function on a protein has been discussed by Kyte and Doolittle (J. Mol. Biol., 157: 105-132, 1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

Since small peptides can be easily produced by conventional solid phase synthetic techniques, the present invention includes peptides, linker regions, and cargo molecules such as those discussed herein, containing the amino acid modifications discussed above, alone or in various combinations. To the extent that such modifications can be made while substantially retaining the cell membrane permeant and targeting properties of the peptide, and the biological function and specificity of the linker region and cargo moieties, they are included within the scope of the present invention. The utility of such modified peptides, linkers, and cargos can be determined without undue experimentation by, for example, the methods described in the examples below.

Linker Regions

Linker regions useful in linking the Tat or other cell membrane-permeant peptides described herein and cargos such as drugs or diagnostic substances such as metal chelator moieties can comprise amino acid residues or substituted or unsubstituted hydrocarbon chains. Useful linker regions include natural and unnatural biopolymers. Examples of natural linkers include oligonucleotides and L-oligopeptides, while examples of unnatural linkers are D-oligopeptides, lipid oligomers, liposaccharide oligomers, peptide nucleic acid oligomers, polylactate, polyethylene glycol, cyclodextrin, polymethacrylate, gelatin, and oligourea (Schilsky, et al., Eds., *Principles of Antineoplastic Drug Development and Pharmacology*, Marcel Dekker, Inc., New York, 1996, pp. 741). The linker region can be designed to be functional or non-functional.

"Non-functional" as applied to linker regions means any non-reactive amino acid sequence, hydrocarbon chain, etc., that can bond covalently to Tat or other cell membrane-permeant peptide residues on one end and a drug or chelating ligand, for example, on the other end. As used herein, the term "non-reactive" refers to a linker that is biologically inert and biologically stable when a complex containing the linker is contacted by cells or tissues. Upon characterization, the linker and conjugate can be shown to remain intact as the parent compound when analyzed by reverse phase HPLC or TLC. Non-functional linkers are desirable in the design and synthesis of complexes useful, for example, in non-specific labeling of white blood cells for imaging infections, in non-specific labeling of tissues for perfusion imaging, and in interaction with any intracellular receptor or other activity or site. Examples of non-functional linkers include, but are not limited to, amino hexanoic acid, glycine, alanine, or short peptide chains of nonpolar amino acids such as di- or tri-glycine or tri-alanine. Hydrocarbon chain linkers can include both unsubstituted and substituted alkyl, aryl, or macrocyclic R groups, as disclosed in U.S. Pat. No. 5,403,574. R groups are found in the general formula —$CR_3$ where R can be identical or different and includes the elements H, C, N, O, S, F, Cl, Br, and I. Representative examples include, but are not limited to, —$CH_3$, —$CH_2CH_3$, —$CH(CH_3)_2$, —$C(CH_3)_3$, —$C(CH_3)_2$, —$OCH_3$, —$C(CH_3)_2$, —$COOCH_3$, —$C(CH_3)_2OCOCH_3$, $CONH_2$, —$C_6H_5$, —$CH_2(C_6H_4)OH$, or any of their isomeric forms. "Alkyl" is intended to mean any straight, branched, saturated, unsaturated or cyclic $C_{1-20}$ alkyl group. Typical $C_1$-$C_{20}$ alkyl groups include, but are not limited to, methyl, ethyl, n-propyl, i-propyl, n-butyl, t-butyl, i-butyl, pentyl and hexyl groups. "Aryl" is intended to mean any aromatic cyclic hydrocarbon based on a six-membered ring. Typical aryl groups include, but are not limited to, phenyl, naphthyl, benzyl, phenethyl, phenanthryl, and anthracyl groups. The term "macrocycle" refers to R groups containing at least one ring containing more than seven carbon atoms. "Substituted" is intended to mean any alkyl, aryl or macrocyclic groups in which at least one carbon atom is covalently bonded to any functional groups comprising the atoms H, C, N, O, S, F, Cl, Br or I.

"Functional" as applied to linker regions means, for example, amino acid residues, oligonucleotides, oligosaccharides, peptide nucleic acids, or substituted or unsubstituted hydrocarbon chains as discussed above that confer biological or physicochemical properties useful for the practice of this invention when incorporated into the linker component. Such properties include, for example, utility in medical imaging, radiotherapy, diagnosis, and pharmacological treatment of disease states by virtue of interaction of the functional linker region with intracellular components, which can be unique to, or highly characteristic of, cells in particular physiological or disease states. Such interaction can include, for example, binding or other reaction, for example cleavage, of the functional linker region due to interaction with intracellular components. However this interaction occurs, such interaction results in selective retention of the cargo molecule within particular cells due to the presence of a particular intracellular component(s) within such cells. The interaction of the functional linker with the intracellular component thereby confers target cell specificity to a peptide complex containing a particular functional linker moiety. Examples of functional linkers are peptide or protein binding motifs, protein kinase consensus sequences, protein phosphatase consensus sequences, or protease-reactive or protease-specific sequences. Additional examples include recognition motifs of exo- and endo-peptidases, extracellular metalloproteases, lysosomal proteases such as the cathepsins (cathepsin B), HIV proteases, as well as secretases, transferases, hydrolases, isomerases, ligases, oxidoreductases, esterases, glycosidases, phospholipases, endonucleases, ribonucleases and β-lactamases.

Specific examples of useful consensus sequences and recognition motifs are: 14-3-3 protein binding motifs such as RSXSphosphoSXP (SEQ ID NO: 8) or RXY/FXphosphoSXP (SEQ ID NO: 9) (Yaffe et al., *Cell,* 91:961-971, 1997). Preferred embodiments include the 14-3-3 protein binding motifs RLSHphosphoSLP (SEQ ID NO: 10), RLYHphosphoSLP (SEQ ID NO: 11) (Peng, et al., Science 277:1501-1505, 1997); and RLSHphosphoSLG (SEQ ID NO: 12). Protease-reactive or specific consensus sequences include, for example, those peptide sequences recognized by interleukin-1β converting enzyme (ICE) homologues, such as caspase-1, CPP32/Yama/apopain/caspase-3, NEDD2/Ich-1/caspase-2, TX/Ich-2/caspase-4, ICE-LAP3/MCH-3/CMH-1/caspase-7, ICE-LAP6/caspase-9, and FLICE/MACH/caspase-8 ((Nakagawara et al. *Cancer Res.,* 57:4578-4584, 1997) and references therein), including YEVDx (SEQ ID NO: 13) for Caspase-1, YDVADx (SEQ ID NO: 14) for Caspase-2, DEVDx (SEQ ID NO: 15) and DMQDx (SEQ ID NO: 16) for Caspase-3, LEVDx ((SEQ ID NO: 17) for Caspase-4, VEIDx (SEQ ID NO: 18) for Caspase-6, DEVDx (SEQ ID NO: 19) for Caspase-7, IETDx (SEQ ID NO: 20) for Caspase-8, and IEADx (SEQ ID NO: 21) for Caspase-10 (Villa, et al., Trends Biochem Sci 22:388-393, 1997); SQVSQNY-PIVQNLQ (SEQ ID NO: 22) for the HIV p17-p24 A cleavage site, and CTERQAN-FLGKIWP (SEQ ID NO: 23) for the HIV p7-p1 D cleavage site (Ratner, et al., Nature 313:277-284, 1985; Welch, et al., Proc Natl Acad Sci USA 88:10792-10796, 1991); xR(R/K)x(S/T)x for Protein Kinase A, x(R/K)$_{2-3}$x(S/T)x for Protein Kinase G, X(R/K$_{1-3}$,x$_{0-2}$)(S/T)(X$_{0-2}$,R/K$_{1-3}$)x for Protein Kinase C, xRxx(S/T)x for Calmodulin Kinase II, KRKQI(S/T)VR (SEQ ID NO: 24) for Phosphorylase b Kinase, TRDIYET-DYYRK (SEQ ID NO: 25) for Insulin Receptor Kinase, and TAENAEYLRVAP (SEQ ID NO: 26) for EGF Receptor Kinase (Kemp and Pearson, Trends Biochem Sci 15:342-346, 1990; Kennelly and Krebs, J Biol Chem 266:15555-15558, 1991). Examples of other useful non-peptide motifs include, for example, DNA recognition sequences such as 3'-TCTTGTnnnACAAGA-5' (SEQ ID NO: 27) for the glucocorticoid hormone response element, 3'-TCCAGT-nnnACTGGA-5' (SEQ ID NO: 28) for the estrogen receptor response element, and 3'-TCCAGTACTGGA-5' (SEQ ID NO: 29) for the thyroid hormone response element (Fuller, FASEB J 5:3092-3099, 1991). Additional sequences known to those skilled in the art and available by reference to public databases can be incorporated into the linker moieties of the present complexes. Well known protein, DNA, and RNA databases available to investigators working in the art of biomedical and pharmaceutical sciences include those linked to the U.S. National Institutes of Health Web Site, such as: http://molbio.info.nih.gov/molbio/, all herein incorporated by reference. A biomolecule or fragment thereof containing a putative recognition motif can be identified by sequence comparison of the primary structure with a primary consensus sequence or individual sequence of a protein or biomolecule in the databases using routine computerized sequence scanning methods such as, for example, BLAST.

When incorporated into the intact Tat or other peptide complexes of the present invention, such sequence motifs will be acted on solely or selectively in those cells containing the appropriate intracellular sequence-specific or sequence-reactive protein, which will alter the intracellular/subcellular distribution and retention of the cargo molecule, e.g., a drug or metal chelate. For example, protease sequences are particularly useful as they result in enzymatic amplification of an imaging or radiotherapeutic effect through enzymatic action on the conjugate complex, thereby cleaving and subsequently trapping metal-chelates within intracellular compartments, leading to an increase in the concentration of the metal-complex fragment.

To further illustrate this principle, if the intracellular target to be detected is a specific protease activity of the caspase family, then when a coordination complex of the present invention comprising the components (Tat peptide)-(caspase-3 motif linker)-(chelate{metal}) translocates into a cell containing caspase-3, the enzyme will cleave the complex in the linker region, thereby releasing the metal-chelate within the cell interior, which can then be monitored by conventional techniques.

Cells or tissues having other biological, biochemical, or physiological activities can also be detected when the appropriate functional linker is incorporated into the covalent or coordination complex. For example, a hexose sequence recognized by β-galactosidase can be synthesized into the linker region of the invention compounds, e.g., as (Tat peptide)-(D-galactose-D-glucose)-(chelate{metal}). Then, upon administration to cells transduced with a marker gene that encodes β-galactosidase, for example in gene therapy, only those cells which express β-galactosidase will cleave and retain the chelate-metal complex for subsequent detection by external imaging devices.

Metal-chelate moieties can be synthesized to possess net charge, for example, by substitution of K for G on the eKGC chelation peptide as illustrated in Example 1. This is useful for in vivo applications in a whole animal. Because non-targeted or unreacted Tat peptide conjugates are capable of bidirectionally translocating across membranes, as the extracellular concentration of a Tat peptide conjugate declines, the intracellular intact Tat peptide conjugate will translocate outwardly and be cleared from the animal via the bloodstream. However, where protease cleavage acts on the peptide, the Tat fragment is separated from the chelate fragment, which further generates a positive charge at the amino-terminus of the cleaved chelate fragment. Thus, the overall charge of the released peptide chelate complex will be polycationic. This cluster of charge combined with the lack of an attached Tat permeation sequence will render the cleaved chelate fragment impermeant to the cell membrane, in effect trapping the chelate fragment within the cell both in vivo and in vitro. In cells lacking the targeted protease activity, the intact Tat peptide-chelate complex translocates outwardly into the extracellular spaces as the extracellular concentration of the Tat peptide decreases. This clearance has been found to occur surprisingly rapidly in vivo. The present invention exploits this high clearance rate to provide high target-to-background ratios for imaging, diagnostics, and therapeutic delivery of metal chelates and drug conjugates to specific cells, tissues and organs.

In cases where the metal-chelate comprises a radioactive metal, then external imaging devices such as scintigraphic gamma cameras or SPECT will only detect high radioactivity within cells, tissues or organs containing the desired biological activity. In contrast, if the metal-chelate comprises a ligand complexed with a relaxivity metal, such as Gd-DTPA, then the resulting enhanced T1 relaxivity would be detectable within cells and tissues of living patients using appropriate T1-weighted pulse sequences generated by clinical magnetic resonance imaging (MRI) devices. Those skilled in the art can readily operate the appropriate MRI device to detect proton relaxivity changes in bodily water induced by relaxivity complexes known as MR contrast agents (Stark and Bradley, Magnetic Resonance Imaging, C.V. Mosby Co., St. Louis, 1988, pp. 1516). Thus, the present invention overcomes a limitation present in existing methods, which do not provide for the intracellular deposition of peptide chelate-metal complexes for targeted medical imaging with SPECT/PET and radiotherapeutic applications, nor allow the interrogation of changes in intracellular proton relaxivity with MRI devices. In contrast, the present invention provides for the intracellular delivery and targeted retention of desired metal complexes.

Other variations are possible wherein the Tat or other peptide-linker-metal complexes contain a functional linker and are sufficiently stable to be delivered to the desired cells and translocated into the cell interior, where they will be acted upon by the targeted intracellular biochemical activity and the retained metal-chelates detected with imaging devices as above.

In addition to radioactive and non-radioactive metals, pharmacologically active substances, prodrugs, cytotoxic substances, and diagnostic substances such as fluorochromes, dyes, enzyme substrates, etc., can be coupled to the linkers of the present membrane-permeant peptide complexes. A wide variety of drugs are suitable for use with the present invention, and include, for example, conventional chemotherapeutics, such as vinblastine, doxorubicin, bleomycin, methotrexate, 5-fluorouricil, 6-thioguanine, cytarabine, cyclophosphamide, taxol, taxotere, cis-platin, adriamycin, mitomycin, and vincristine as well as other conventional chemotherapeutics as described in *Cancer: Principles and Practice of Oncology*, 5th Ed., V. T. Devita, S. Hellman, S. A. Rosenberg, J. B. Lippincott, Co., Phila, 1997, pp. 3125. Also suitable for use in the present invention are experimental drugs, such as UCN-01, acivicin, 9-aminocamptothecin, azacitidine, bromodeoxyuridine, bryostatin, carboplatin, dideoxyinosine, echinomycin, fazarabine, hepsulfam, homoharringtonine, iododeoxyuridine, leucovorin, merbarone, misonidazole, pentostatin, semustine, suramine, mephthalamidine, teroxirone, triciribine phosphate and trimetrexate as well as others as listed in *NCI Investigational Drugs, Pharmaceutical Data* 1994, NIH Publications No. 94-2141, revised January 1994.

Other useful drugs include anti-inflammatories such as Celebrex, indomethacin, flurbiprofen, ketoprofen, ibuprofen and phenylbutazone; antibiotics such as beta-lactams, aminoglycosides, macrolides, tetracyclines, pryridonecarboxylic acids and phosphomycin; amino acids such as ascorbic acid and N-acetyltryptophan; antifungal agents; prostaglandins; vitamins; steroids; and antiviral agents such as AZT, DDI, acyclovir, gancyclovir, idoxuridine, amantadine and vidarabine.

Pharmacologically active substances that can be conjugated to the complexes of the present invention include, but are not limited to, enzymes such as transferases, hydrolyses, isomerases, proteases, ligases, kinases, and oxidoreductases such as esterases, phosphatases, glycosidases, and peptidases; enzyme inhibitors such as leupeptin, chymostatin and pepstatin; and growth factors.

In addition, the present invention can be used to deliver fluorochromes and vital dyes into cells. Examples of such fluorochromes and vital dyes are well known to those skilled in the art and include, for example, fluorescein, rhodamine, coumadin, indocyanine Cy 5.5, NN382, Texas red, DAPI and ethidium bromide.

The delivery of drug and pharmacologically active compounds into the cell interior can be enhanced by direct conjugation to the Tat or other membrane-permeant peptides of the present invention. The coupling of such compounds to a functional linker placed between a D-amino acid containing cell membrane-permeant peptide and the active agent, thereby enabling enhanced, functionally selective, intracellular trapping of the drug or drug conjugate, is new. A drug or prodrug conjugate designed as described herein would enable selective delivery (and retention) of bioactive agents and therapeutic or biologic enhancers useful in therapy including, but not limited to, granulocyte-stimulating factors, platelet-stimulating factors, erythrocyte-stimulating factors, macrophage-colony stimulating factors, interleukins, tumor necrosis factors, interferons, other cytokines, monoclonal antibodies, immune adjuvants and gene therapy vectors (Devita, et al., *Biologic Therapy of Cancer,* 2nd Ed., J. B. Lippincott, Co., Phila, 1995, pp. 919), and drugs into the cell interior in a manner analogous to the selective trapping of metal chelates as described above. Linker functionality can include any motif that can be acted on by a specific intracellular agent, such as the enzymes discussed above, or ribozymes, for example. Examples of such linker functionalities include low molecular weight peptide or protein binding motifs, protein kinase consensus sequences, protein phosphatase consensus sequences, or protease-specific sequences. As explained previously, protease-reactive or protease-specific sequences are particularly useful in that amplification of the therapeutic effect would occur through enzymatic action on the linker region of the drug or prodrug conjugate, thereby releasing the pharmacological agent in the cell cytosol, and increasing the intracellular retention and concentration of the agent.

Pharmacologically active substances, cytotoxic substances, diagnostic substances, etc., can be coupled to the appropriate cell membrane-permeant peptide-linker conjugate through either the amino- or carboxy-terminus of the linker region in a manner analogous to that described in Example 1. For example, drug conjugates wherein the carboxy-terminus of the peptide linker is coupled to a bioactive substance can be prepared by the use of an active ester of the desired bioactive substance in the presence of a dehydrating agent. Examples of active esters that can be used in the practice of the present invention include the hemi-succinate esters of N-hydroxysuccinimide, sulfo-N-hydroxy-succinimide, hydroxybenzotriazole, and p-nitrophenol. Dehydration agents include dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI). The use of ECD to form conjugates is disclosed in U.S. Pat. No. 4,526,714, the disclosure of which is fully incorporated by reference herein. Other examples of coupling reagents include glutathione, 3-(diethoxyphosphoryloxy)-1,2,3-benzotriazin-4(3H)-one (DEPBT), onium salt-based coupling reagents, polyoxyethylene-based heterobifunctional cross-linking reagents, and other reagents that facilitate the coupling of organic drugs and peptides to various ligands (Haitao, et al., *Organ Lett* 1:91-94, 1999; Albericio, et al., *J Organic Chemistry* 63:9678-9683, 1998; Arpicco, et al., *Bioconjugate Chem* 8:327-337, 1997; Frisch, et al., *Bioconjugate Chem* 7:180-186, 1996; Deguchi, et al., *Bioconjugate Chem* 10:32-37, 1998; Beyer, et al., *J Med Chem* 41: 2701-2708, 1998; Dirven, et al., *Chem Res Toxicol* 9:351-360, 1996; Drouillat, et al., *J Pharm Sci* 87:25-30, 1998; Trimble, et al., *Bioconjugate Chem* 8:416-423, 1997). Chemicals, reagents and techniques useful in drug cross-linking and peptide conjugation are disclosed in general texts well known to those skilled in the art (Dawson, et al., (Eds.), *Data for Biochemical Research*, 3rd Ed., Oxford University Press, Oxford, UK, 1986, pp. 580; King, (Ed.), *Medicinal Chemistry: Principles and Practice*, Royal Society of Chemistry, Cambridge, UK, 1994, pp. 313; Shan and Wong, (Eds.), *Chemistry of Protein Conjugation and Cross-Linking*, CRC Press, Boca Raton, 1991, pp. 328). Additional chemical coupling agents are described in U.S. Pat. No. 5,747,641, hereby incorporated by reference in its entirety.

Conjugated Chelate Ligands and Drugs

The present invention also encompasses the use of chelation ligands to form coordinate bonds with desired metals. The desired chelation ligands are attached to the peptide conjugate where they bind radionuclides and desired non-radioactive metals in a highly efficient and stable manner. When the metal is a radionuclide, this allows the reporting of the spatial location of the conjugate with external imaging devices such as SPECT and PET detectors following administration of the conjugate to an animal. As disclosed above, preferred embodiments of the present invention permit the chelation moiety to be concentrated within cellular and tissue compartments in proportion to specific enzymatic or protein activities present in the cells therein. In other preferred embodiments, where the metal is a selected therapeutic radionuclide, the present invention allows the chelation moiety to be concentrated within target cellular and tissue compartments in proportion to a specific enzymatic or protein activity to deposit radiation selectively within the target cell or tissue. In another preferred embodiment, when the metal is a relaxivity metal, the chelation moiety permits magnetic resonance imaging of the cell or tissue. Alternatively, when the functional linker region of the permeant peptide construct is conjugated to a drug, the drug will be selectively deposited within the target cell or tissue by methods of this invention.

Suitable chelation ligands are well known to those skilled in the art and include, but are not limited to, diethylenetriaminepentaacetic acid (DTPA), ethylenediaminetetraacetic acid (EDTA), tetraazacyclododecanetetraacetic acid (DOTA), and other chelators that incorporate electron donating atoms such as O, S, P or N as Lewis bases to bind the metal (Engelstad and Wolf, "Contrast Agents", in *Magnetic Resonance Imaging*, Stark and Bradley, Mosby, St. Louis, 1988, pp. 161-181). The present complexes can also employ chelating ligands such as, but not restricted to, those containing $N_2S_2$, $N_3S$, $N_2SO$ and $NS_3$) moieties (Meegalla et al., *J. Med. Chem.*, 40:9-17, 1997). Specific examples (as shown below) wherein these chelation moieties are incorporated into specific sequences of peptide residues, such as E-amine modified Lys-Gly-Cys tags, are especially convenient for synthesizing the desired chelation groups directly into peptide-based sequences. Preferred chelation ligands are peptides or modified peptides which enable the chelation moiety to be incorporated into the peptide construct directly by solid phase synthesis by use of appropriately blocked peptide precursors compatible with commercial peptide synthesizers. Examples of this preferred embodiment are illustrated below in more detail. Alternatively, other preferred chelation ligands can be chemically coupled to the peptide conjugate by use of one or more of the linker reagents described above. Other preferred embodiments of the invention encompass the conjugation of drugs to the functionalized linker region attached to the permeant peptide. In one embodiment, the chelation complexes of the present invention comprise a peptide-based chelator wherein the coordination sites of the chelator are filled with a metal useful in imaging or radiotherapy.

Radioactive and Non-Radioactive Metals

Useful metals for chelation into the complexes of the present invention include radionuclides having decay properties that are amenable for use as a diagnostic tracer or for deposition of medically useful radiation within cells or tissues. The present invention consequently encompasses the use of conjugated coordination complexes of a ligand with a radioactive metal (radionuclide). The radioactive nuclide can, for example, be selected from the group consisting of radioactive isotopes of Tc, Ru, In, Ga, Co, Pt, Fe, Os, Ir, W, Re, Cr, Mo, Mn, Ni, Rh, Pd, Nb, Cu and Ta, for example, Tc-99m, Tc-99, In-111, Ga-67, Ga-68, Cu-64, Ru-97, Cr-51, Co-57, Re-188, and Re-186. Such complexes can be used for medical imaging and specifically for SPECT or PET imaging, as provided herein. Technetium-99m (Tc-99m; t ½=6 hours; 140 keV emission photon) is the most commonly used radionuclide in diagnostic nuclear medicine (Jurisson et al., *Chem. Rev.*, 93:1137-156, 1993). It can be readily produced by molybdenum-99/technetium-99m generators available in clinical nuclear medicine radiopharmacy laboratories, and has favorable emission characteristics that enable ready detection with clinical gamma cameras. While the complexes of the present invention preferably contain Tc-99m and the closely related rhenium isotopes (Re-186 and Re-188), other radionuclides and metals, in addition to those already listed, useful for imaging and radiotherapy such as I-123, I-125, I-130, I-131, I-133, Sc-47, As-72, Se-72, Y-90, Y-88, Pd-100, Rh-100m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199 are also encompassed within the scope of this invention. Moreover, the general availability of supplies of pertechnetate from a variety of vendors makes it convenient to use kits for preparation of various peptide complexes of Tc-99m. Labeling of the peptide conjugates of the present invention with radioactive metals can be readily performed. In preferred embodiments of this invention, the peptide conjugate is radiolabeled with $^{99m}$Tc using standard reducing agents with or without transmetallation reactions (Grummon, et al., *Inorg Chem* 34:1764-1772, 1995; Lister-James, et al., *J Nucl Med* 37:775-781, 1997; Meegalla, et al., *J Med Chem* 40:9-17, 1997).

Useful metals also include isotopes of those metals possessing paramagnetism which produce water relaxation properties useful for generating images with magnetic resonance imaging (MRI) devices. Suitable relaxivity metals include, but are not limited to, Mn, Cr, Fe, Gd, Eu, Dy, Ho, Cu, Co, Ni, Sm, Tb, Er, Tm, and Yb. Appropriate chelation ligands to coordinate MR relaxivity metals can be readily incorporated into the peptide complexes of this invention by the methods previously described for radionuclides. Such chelation ligands can include, but are not limited to, DTPA, EDTA, DOTA, TETA, EHPG, HBED, ENBPI, ENBPA, and other macrocycles known to those skilled in the art (Stark and Bradley, *Magnetic Resonance Imaging*, C. V. Mosby Co., St Louis, 1988, pp 1516).

The peptide metal coordination complexes of the present invention can be readily prepared by methods known in the art. For example, a Tat or other cell membrane-permeant peptide conjugated to a linker and a metal chelating moiety can be admixed with a salt of the radioactive metal in the presence of a suitable reducing agent, if required, in aqueous media at temperatures from room temperature to reflux temperature, and the end-product coordination complex can be obtained and isolated in high yield at both macro (carrier added, e.g., Tc-99) concentrations and at tracer (no carrier added, e.g., Tc-99m) concentrations (typically less than $10^{-6}$ molar). It is well established that when (Tc-99m) pertechnetate ($TcO_4^{31}$) is reduced by a reducing agent, such as stannous chloride, in the presence of chelating ligands such as, but not restricted to, those containing $N_2S_2$, $N_2SO$, $N_3S$ and $NS_3$ moieties, complexes of $(TcO)N_2S_2$, $(TcO)N_2SO$, $(TcO)N_3S$ and $(TcO)NS_3$ are formed (Meegalla et al. *J. Med. Chem.*, 40:9-17, 1997). Another preferred method for radio labeling the peptide involves the use of glucoheptonate together with a reducing agent such as stannous chloride to label the chelation moiety on the peptide (Lister-James, et al., *J Nucl Med* 37:775-781, 1997; Meegalla, et al., *J Med Chem* 40:9-17, 1997). Another preferred labeling method involves one-step labeling of His-tagged peptides with Tc(I)-carbonyl complexes (Waibel, et al., *Nature Biotechnology*, 17:897-901, 1999). Such Tc-99m labeling and chelating moieties can be incorporated into potential receptor-selective imaging agents (Horn and Katzenellenbogen, *Nucl. Med. Biol.*, 24:485-498, 1997). The incorporation of such moieties, specifically those that chelate radioactive metals or other metals of interest for imaging (e.g., magnetic resonance relaxivity metals) or radiotherapy, into the Tat or other peptide motif via the use of a functional linker, thereby enabling selective intracellular delivery and retention of the metal coordination complex, is new. Non-radioactive metals useful for MR imaging can be incorporated into an appropriate chelator useful for binding relaxivity metals which in turn has been conjugated onto the peptide linker construct as described above. A preferred embodiment of this invention is the coupling of DOTA to the peptide conjugate using methods referenced above and using Gd as the MR relaxivity metal. Gd can be chelated into the DOTA moiety by reaction of chloride salts of Gd, such as $GdCl_3$, with the peptide chelate conjugate under mildly acidic conditions (pH 5-6) using standard techniques (Stark and Bradley, *Magnetic Resonance Imaging*, C. V. Mosby Co., St. Louis, 1988, pp. 1516; Wen-hong, et al., *J Am Chem Soc* 121:1413-1414, 1999).

Other Applications

The present complexes can also be used in fluorescence resonance energy transfer (FRET) to study intracellular processes. When used with the FRET methodology, the functional linker is placed between the fluorescent energy donor and acceptor. Examples of suitable pairs of fluorescent energy donor and acceptors, as well as methods for using FRET, are well known in the art and are described, for example, in Ubarretxena-Belandia et al., *Biochemistry*, 38:7398-7405, 1999; Blomberg et al., *Clin. Chem.*, 45:855-861, 1999; and Jamieson et al., *J. Biol. Chem.* 274:12346-12354, 1999. Near infrared fluorescent (NIRF) probes may also be appended on each side of the linker such that when the linker is intact, the probes are autoquenched and, when the linker is specifically cleaved, the NIRF probes fluoresce (Tyagi et al., *Nature Biotech.*, 14:303-308, 1996).

In addition to providing compositions and methods for medical imaging, other diagnostic methods, and drug delivery, the present invention also provides methods for evaluating intracellular processes in living cells in vivo and in tissues in vitro. Examples of such processes include protein-protein binding, protein kinase activities, protein phosphatase activities, or protease activities. Additional examples include the activities of exo- and endo-peptidases, extracellular metalloproteases, lysosomal proteases such as the cathepsins (cathepsin B), as well as α-, β-, and γ-secretases, transferases, hydrolases, isomerases, ligases, oxidoreductases, esterases, glycosidases, phospholipases, endonucleases, ribonucleases and β-lactamases as they relate to the various disease states associated with loss of function or gain of function for each. These methods are performed by administering agents that are translocated across the plasma membrane into cells and which are detectable in living cells despite the presence of biological tissue intervening between the detection device and the cells in their in situ location. Thus, cells in the living body or in a tissue mass are detectable in situ.

In accordance with the present invention, living cells can be imaged. Complexes of this invention useful in generating images are administered to a patient, or to cells or a tissue specimen. Imaging procedures include, but are not limited to, magnetic resonance imaging (MRI), superconducting quantum interference device (SQUID), near infrared imaging, optical fluorescence imaging, positron emission tomography (PET), and, in highly preferred embodiments, imaging is by planar scintigraphy or single photon emission computed tomography (SPECT).

These methods are also applicable to rapid and simple assays of intracellular biochemical reactions in vitro and, more importantly, as assays in instances in which presently available assay methods are impractical or impossible, such as in vivo and in situ. For example, in excised tissues, intracellular functions include biochemical activities such as protein-protein binding, protein kinase activities, protein phosphatase activities, and protease activities. Additional examples include the activities of exo- and endo-peptidases, extracellular metalloproteases, lysosomal proteases such as the cathepsins (cathepsin B), as well as that of α-, β-, and γ-secretases, transferases, hydrolases, isomerases, ligases, oxidoreductases, esterases, glycosidases, phospholipases, endonucleases, ribonucleases and β-lactamases, which can be detected without the need for tissue dispersion and growth that change the in vivo phenotype. These methods are especially valuable for in vivo assays whereby intracellular biological activities are detected without the need for traumatic surgery.

By the use of the present methods, intracellular functions can be detected in patients without the need for surgery. Accordingly, the present invention encompasses compounds and methods for detecting intracellular biochemical activities in living, whole animals, tissues, or cells by administering complexes of this invention which translocate into cells, and which are detectable in living cells at distances removed from the cells by the presence of intervening tissue. Examples of tissues to which the methods of the present invention can be applied include, for example, cancer cells, in particular, central nervous system tumors, breast cancer, liver cancer, lung, head and neck cancer, lymphomas, leukemias, multiple myeloma, bladder cancer, ovarian cancer, prostate cancer, renal tumors, sarcomas, colon and other gastrointestinal cancers, metastases, and melanomas. More specifically, the present invention can be applied to cancers such as sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. The present invention can also be used to detect the presence of enzymes associated with diseases, conditions or disorders. Examples of diseases, conditions or disorders to which the present invention can be applied include, but are not limited to infection, inflammation, neurodegenerative diseases such as Alzheimer's disease and Parkinson's disease, ALS, hypoxia, autoimmune diseases, immune deficiencies, cardiovascular insults such as infraction and stroke, and connective tissue disorders such as rheumatoid arthritis, lupis and dermatomyositis, and other specific dysfunctions of organs. Enzyme(s) associated with particular diseases, conditions, or disorders are well known to those skilled in the art and can be found in standard medical references, for example, *Stedman's Medical Dictionary*, 26th Edition, Williams & Wilkins, 1995, and *Harrison's Principles of Internal Medicine*, 14th Edition, McGraw-Hill, 1998. The present invention therefore encompasses peptide conjugate metal coordination complexes (and other diagnostically useful complexes) and methods of detecting such complexes or their reaction products in living, whole animals, tissues, or cells by administering the present imaging complexes, especially a scintigraphic or magnetic resonance imaging complex, which translocates into the interior of living cells.

Kits

The present invention also provides kits comprising a quantity of a reducing agent for reducing a preselected radionuclide, as described, for example, by Jones et al., U.S. Pat. No. 4,452,774. Such kits can contain a predetermined quantity of a Tat or other cell-permeant peptide conjugate and a predetermined quantity of a reducing agent capable of reducing a predetermined quantity of a preselected radionuclide. Such kits can contain a predetermined quantity of glucoheptonate. The peptide conjugate and reducing agent can be lyophilized to facilitate storage stability. The conjugate and reducing agent can be contained in a sealed, sterilized container. Instructions for carrying out the necessary reactions, as well as a reaction buffer solution(s), can also be included in the kit.

In one embodiment, the present invention provides a kit for use in preparing cell membrane-permeant coordination complexes from a supply of Tc-99m such as pertechnetate solution in isotonic saline available in clinical nuclear medicine laboratories, including the desired quantity of a selected Tat or other peptide conjugate to react with a selected quantity of pertechnetate, and a reducing agent such as sodium dithionite or stannous chloride in an amount sufficient to reduce the selected quantity of pertechnetate to form the desired peptide metal complex. In a preferred embodiment, the kit includes a desired quantity of a selected peptide conjugate to react with a selected quantity of reduced technetium supplied in the kit in the form of Tc-99m-glucoheptonate, itself produced from a stannous glucoheptonate commercial kit (Dupont Pharma), and a reducing agent such as sodium dithionite or stannous chloride in an amount sufficient to assure that the selected quantity of reduced technetium produces the desired peptide metal complex.

Pharmaceutically Acceptable Salts of Peptide Complexes

Like amino acids, peptides and proteins are ampholytes, i.e., they act as both acids and bases by virtue of the presence of various electron-donor and acceptor moieties within the molecule. The peptide complexes of the present invention can therefore be used in the free acid/base form, in the form of pharmaceutically acceptable salts, or mixtures thereof, as is known in the art. Such salts can be formed, for example, with organic anions, organic cations, halides, alkaline metals, etc.

The term "pharmaceutically acceptable salts" embraces salts commonly used to form alkali metal salts and addition salts of free acids or free bases. The nature of the salt is not critical, provided that it is pharmaceutically acceptable. Suitable pharmaceutically acceptable base addition salts of the present peptide complexes include metallic salts and organic salts.

Preferred metallic salts include, but are not limited to, appropriate alkali metal (group Ia) salts, alkaline earth metal (group IIa) salts, and other physiologically acceptable metals. Such salts can be prepared, for example, from aluminum, calcium, lithium, magnesium, potassium, sodium, and zinc.

Organic salts can be prepared from tertiary amines and quaternary ammonium salts, including in part, tromethamine, diethylamine, N,N'-dibenzyl-ethylenediamine, chloroprocaine, choline, diethanolamine, ethylenediamine, meglumine (N-methyl-glucamine), and procaine.

Such salts can also be derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others.

All of these salts can be prepared by conventional means from the corresponding peptide complex disclosed herein by reacting the appropriate acid or base therewith. Water- or oil-soluble or dispersible products are thereby obtained as desired.

Formulations/Pharmaceutical Compositions

The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., *Remington's Pharmaceutical Sciences*, Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables.

Dimethyl acetamide, surfactants including ionic and nonionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Doses/Quantities of Peptide Complexes

The quantity of cell membrane-permeant peptide complex comprising a radionuclide for use in radiolabelling and imaging, or relaxivity metal, should be an effective amount for the intended purpose. Such amounts can be determined empirically, and are also well known in the art. For example, amounts of radio nuclide administered via the present complexes can be in the range of from about 1 µCi to about 100 mCi, preferably from about 1 mCi to about 100 mCi, and more preferably from about 1 mCi to about 50 mCi. This amount can be adjusted for body weight and the particular disease state, and can be about 1 mCi/kg body weight.

For therapeutic purposes, the amount of radio nuclide administered via the present complexes can be in the range of from about 1 mCi to about 300 mCi, preferably from about 25 mCi to about 250 mCi, and more preferably from about 50 mCi to about 200 mCi. Of course, this amount can be tailored to meet the specific requirements of the disease state being treated, and can also vary depending upon the weight and condition of the patient as is well known in the art. Note, for example, *Clinical Nuclear Medicine,* 1998, Third Edition, Chapman & Hall Medical.

The amount of complex comprising a drug or other pharmacologically active agent for administration to a patient to treat or prevent a disease condition will vary with the type of drug, and will comprise a therapeutically effective amount thereof. Drug dosages for treating various conditions are well known in the art. Note in this regard, for example, *Goodman & Gilman's The Pharmacological Basis of Therapeutics,* 1996, Ninth Edition, McGraw-Hill, New York.

Routes of Administration

The complexes of the present invention can be administered by a variety of methods, including, for example, orally, enterally, mucosally, percutaneously, or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the complexes can be administered by means of micro-encapsulated preparations, for example those based on liposomes as described in European Patent Application 0 213 523.

Treatment Regimens

The regimen for treating a patient with the compounds and/or compositions of the present invention is selected in accordance with a variety of factors, including the age, weight, sex, diet, and medical condition of the patient, the severity of the condition, the route of administration, pharmacological considerations such as the activity, efficacy, pharmacokinetic, and toxicology profiles of the particular pharmacologically active compounds employed.

Administration of the drug complexes disclosed herein should generally be continued over a period of several days, weeks, months, or years. Patients undergoing treatment with the drug complexes disclosed herein can be routinely monitored to determine the effectiveness of therapy for the particular disease or condition in question.

Continuous analysis of the data obtained by these methods permits modification of the treatment regimen during therapy so that optimal amounts of the pharmacologically active substance in the peptide complex are administered, and so that the duration of treatment can be determined as well. Thus, the treatment regimen/dosing schedule can be rationally modified over the course of therapy so that the lowest amounts of drug compound is administered, and so that administration of such compounds is continued only so long as is necessary to successfully treat the disease or condition.

Monitoring Devices/Procedures

Detection methods useful in practicing the present invention include, but are not limited to magnetic resonance, superconducting quantum interference device (squid), optical imaging, positron emission tomography, and in particular, planar scintigraphy or single photon emission computed tomography (SPECT). Alternative methods of detection include gamma counting, scintillation counting, scanning radiograms, densitometry and fluorography. These detection methods can be employed during or after an effective time interval for diagnosis or imaging subsequent to administering a peptide complex of the present invention. Such effective time intervals are well known in the art, or can be determined by routine experimentation employing methods such as those disclosed herein.

Although the examples hereinafter provided contain many specificities, these should not be construed as limiting the scope of the invention, but as merely providing illustrations of some of the aspects of the present invention.

EXAMPLE 1

Preparation of acetyl-GRKKRRQRRR-AHA-εKGC-amide trifluoroacetate

A Tat peptide (residues 48-57, GRKKRRQRRR (SEQ ID NO: 7)) conjugate was prepared by solid phase peptide synthesis using N-α-FMOC-protected amino acids and standard BOP/HOBt coupling chemistry (Merifield et al., *Biochemistry* 21:5020-5031, 1982; Houghten, *Proc Natl Acad Sci USA* 82:5131-5135, 1985; Lin, et al., *Biochemistry* 27:5640-5645, 1988), except for the ε-Lys residue, which used an N-α-tBOC, N-ε-FMOC-Lys residue to generate the desired peptide-based $N_3S$ chelating group for an incoming metal (Lister-James, et al., *Q J Nucl Med* 41:111-118, 1997). AHA represents aminohexanoic acid as an example of a non-functional linker between the Tat 48-57 residues and the chelating moiety. The peptide was amino acetylated, carboxy amidated, and deprotected by standard methods (Merifield et al., *Biochemistry* 21:5020-5031, 1982; Houghten, *Proc Natl Acad Sci USA* 82:5131-5135, 1985; Lin, et al., *Biochemistry* 27:5640-5645, 1988). The peptide was purified (>94%) by preparative $C_{18}$ reversed-phase HPLC using as eluent 0.1% trifluoroacetic acid in water (0.1% $TFA/H_2O$) modified with 0.1% trifluoroacetic acid in 90% acetonitrile/10% water (0.1% $TFA/(90\% CH_3CN/H_2O)$) by a linear gradient (0% to 60% over 60 min) (peptide $R_t$=21 min). The identity of the peptide conjugate was confirmed by amino acid analysis (13 proteinogenic amino acids: Glu 1; Gly 2; Cys 1; Lys 3, Arg 6) and electrospray mass spectrometry (m/z: 1839.0; calc: $C_{74}H_{143}N_{37}O_{16}S_1$, 1839.27). The sequence was confirmed as acetyl-GRKKRRQRRR-AHA-εKGC-amide ((SEQ ID NO: 30).

EXAMPLE 2

Figure 2:
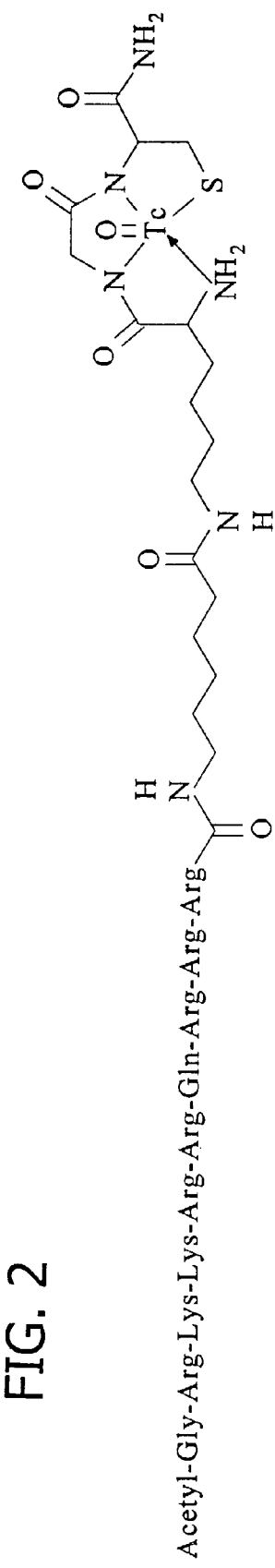
FIG. 2 shows the proposed structure of an oxotechnetium-Tat-peptide complex. The coordination metal ($Tc^vO$) may be replaced by $Re^vO$ to form essentially isostructural complexes.

Preparation of Radiolabeled acetyl-GRKKRRQRRR-AHA-εKGC-amide(Tc$^v$-99m) trifluoroacetate The Tat peptide conjugate complex of Example 1 was labeled with Tc-99m by ligand exchange using Tc-99m-glucoheptonate as the ligand exchange reagent (Lister-James et al., *J. Nucl. Med.* 38:105-111, 1997). A commercially available stannous glucoheptonate radiopharmaceutical kit (Glucoscan, DuPont Pharma, Billerica, Mass.) was reconstituted with 1.0 ml of (Tc-99m)sodium pertechnetate (50 mCi) in isotonic saline obtained by eluting a commercial radionuclide Mo-99/Tc-99m generator, and allowed to stand for 15 min at room temperature. In a small glass vial, Tat peptide conjugate (1 mg) was dissolved in 0.9% saline (1 ml). Then, (Tc-99m)glucoheptonate (250 μl) was added and the reaction allowed to proceed at room temperature for 15 min. Radiochemical yield (>95%) of the oxotechnetium complex (FIG. 2) and purity (≧90%) were determined by silica gel TLC using 15% TFA and radiometric detection (Bioscan)((Tc-99m)-peptide complex, $R_f$ 0.24; (Tc-99m)-glucoheptonate, $R_f$ 0.95; (Tc-99m)-$TcO_4^-$, $R_f$ 0.95).

EXAMPLE 3

Preparation of acetyl-GRKKRRQRRR-AHA-εKGC-amide-fluorescein-maleimide trifluoroacetate The Tat peptide conjugate of Example 1 was labeled with fluorescein according to Vives et at. (*J. Biol. Chem.*, 272: 16010-16017, 1997). In a small glass vial, Tat peptide conjugate (1 mg) was dissolved in phosphate buffered saline (pH 7.4) and reacted with 1.2 eq of fluorescein maleimide dissolved in dimethylformamide for 2 hours in the dark at room temperature. The reaction was monitored by RP-HPLC at both 211 nm and 440 nm. Fluorescent peptides were purified by HPLC (purity >97%) using the above gradient conditions and lyophilized in the dark. The identity of the desired fluorescein labeled peptide was confirmed by electrospray mass spectrometry (m/z: 2211.0).

EXAMPLE 4

Solutions for Cell Uptake Experiments

Control solution for cell uptake experiments was a modified Earle's balanced salt solution (MEBSS) containing (mM): 145 $Na^+$, 5.4 $K^+$, 1.2 $Ca^{2+}$, 0.8 $Mg^{2+}$, 152 $Cl^-$, 0.8 $H_2PO_4^-$, 0.8 $SO_4^{2-}$, 5.6 dextrose, 4.0 HEPES, and 1% bovine calf serum (vol/vol), pH 7.4±0.05. A 130 mM $K^+$/20 mM $Cl^-$ solution was made by equimolar substitution of potassium methanesulfonate for NaCl as described by Piwnica-Worms et al. (*J. Gen. Physiol*, 81:731-748, 1983).

EXAMPLE 5

Cell Culture

Monolayers of human epidermoid carcinoma KB 3-1 cells and the colchicine-selected KB 8-5 and KB 8-5-11 derivative cell lines were grown as previously described (Akiyama et al., *Somatic Cell Mol. Genet.*, 11:117-126, 1985; Piwnica-Worms et al., *Cancer Res.*, 53:977-984, 1993). Briefly, cells were plated in 100-mm Petri dishes containing seven 25-mm glass coverslips on the bottom and grown to confluence in DMEM (GIBCO, Grand Island, N.Y.) supplemented with L-glutamine (1%), penicillin/streptomycin (0.1%), and heat-inactivated fetal calf serum (10%) in the presence of 0, 10 and 100 ng/ml colchicine, respectively. Human Jurkat leukemia cells and Hela tumor cell lines were maintained in RPMI supplemented with 5-10% fetal calf serum, penicillin, streptomycin, and L-glutamine at 37° C. in an atmosphere of 5% $CO_2$ (Peng et al., *Science*, 277:1501-1505, 1997).

EXAMPLE 6

Cell Accumulation and Washout Studies of Tat-Peptide Conjugate Metal Complexes

Coverslips with confluent cells were used for studies of cell transport and kinetics of labeled Tat peptide conjugate complexes as previously described (Piwnica-Worms et al., *Cancer Res.*, 53:977-984, 1993). Cells were removed from culture media and pre-equilibrated for 15-30 seconds in control buffer. Accumulation experiments were initiated by immersing coverslips in 60-mm glass Pyrex dishes containing 4 ml of loading solution consisting of MEBSS with 7 nM to 8 µM of the peptide conjugate of Example 2 (1-2 µCi/ml). Coverslips with cells were removed at various times, rinsed three times in 25 ml ice-cold isotope-free solution for 8 seconds each to clear extracellular spaces, and placed in 35-mm plastic Petri dishes. Cells were extracted in 1% sodium dodecylsulfate with 10 mM sodium borate before protein assay by the method of Lowry (Lowry et al. *J. Biol. Chem.*, 193:265-275, 1951) (KB cells) or by BCA analysis (pierce Chemical Co.) using bovine serum albumin as the protein standard. Aliquots of the loading buffer and stock solutions also were obtained for standardizing cellular data with extracellular concentration of each Tc-complex. Cell extracts, stock solutions, and extracellular buffer samples were assayed for gamma activity in a well-type sodium iodide gamma counter (Cobra II, Beckman). The absolute concentration of total Tc-complex in solution was determined from the peptide stock solutions and specific activity of technetium, based on equations of Mo/Tc generator equilibrium (Lamson et al., *J. Nucl. Med.*, 16:639-641, 1975).

Characterization of accumulation of Tc-99m-peptide complex was also performed for nonadherent cell lines such as human Jurkat leukemia cells with minor modifications of methods described in the literature (Bosch et al., *Leukemia*, 11: 1131-1137, 1997). Transport experiments were performed in siliconized microfuge tubes and initiated by addition of 732.5 µl of cells at 2-3×10$^6$ cells/ml to 10 µl of buffer containing Tc-99m-peptide complex and 7.5 µl of vehicle alone or of any added drug in vehicle at 100-fold the desired concentration. The tubes were incubated in a 37° C. water bath with occasional mixing. The reaction was terminated by centrifuging 250 µl aliquots from the reaction for 10 seconds through 800 µl of a 75:25 mixture of silicon oil, density=1.050 (Aldrich) and mineral oil, density=0.875 (Acros). An aliquot of the aqueous phase was obtained to normalize extracellular concentration of the complex to cell-associated activity, then the oil and aqueous phases were aspirated and the cell pellet extracted in 0.5 ml of 1% SDS, 10 mM sodium borate. For tracer washout experiments, cells were first incubated to plateau uptake (10 min) in loading buffer (37° C.), collected by rapid centrifugation and the pellet resuspended in 50 ml MEBSS (4° C.) to clear extracellular tracer. Following another rapid spin, the cell pellet was resuspended in isotope-free MEBSS (37° C.) and the experiment terminated as above after various times in warm washout buffer. Radioactivity of the cell pellet, buffers and stocks were determined on a gamma counter (Cobra II, 130-165 keV window) and cell protein was determined by the BCA assay (Pierce). Transport data are reported as fmol Tc-complex (mg protein)$^{-1}$ (nM$_0$)$^{-1}$ as previously described, with (nM$_0$)$^{-1}$ representing total concentration of peptide conjugate in the extracellular buffer (Piwnica-Worms et al., *Circulation*, 82: 1826-1838, 1990).

Figure 3:
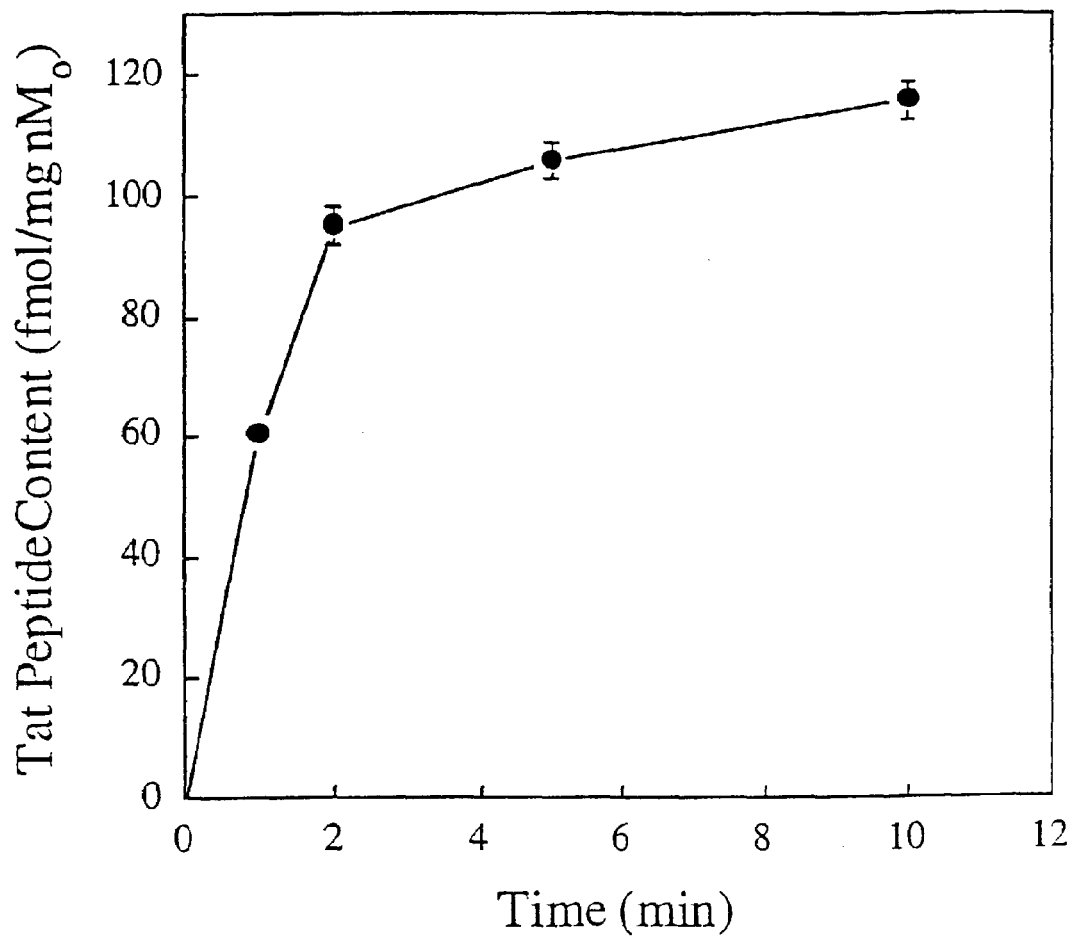
FIG. 3 shows the time course of cellular uptake of a Tc-99m-Tat peptide complex in human Jurkat cells. Extracellular concentration of peptide was 950 nM. Each point represents the mean of 4 observations±SEM when larger than the symbol. Cell accumulation of the Tc-99m-Tat peptide complex is 90% complete within 2 minutes and established a quasi-steady state that was maintained for at least 1 hour (data not shown).

When exposed to radioactive Tc-99m-Tat peptide metal complex, human Jurkat leukemia cells rapidly accumulated the complex, approaching a plateau within 2 minutes (FIG. 3). Steady-state values for the Tc-99m-Tat peptide metal complex in Jurkat cells was 116±13 fmol (mg protein)$^{-1}$ (nM$_0$)$^{-1}$ (n=4). Given a typical cell water space of 4 µl (mg protein)$^{-1}$, this would indicate an in/out ratio for the complex of ~30, directly demonstrating that the complex is rapidly and highly concentrated within cells. When continuously exposed to the complex, cells were observed to maintain this plateau for at least 1 hour.

Figure 4:
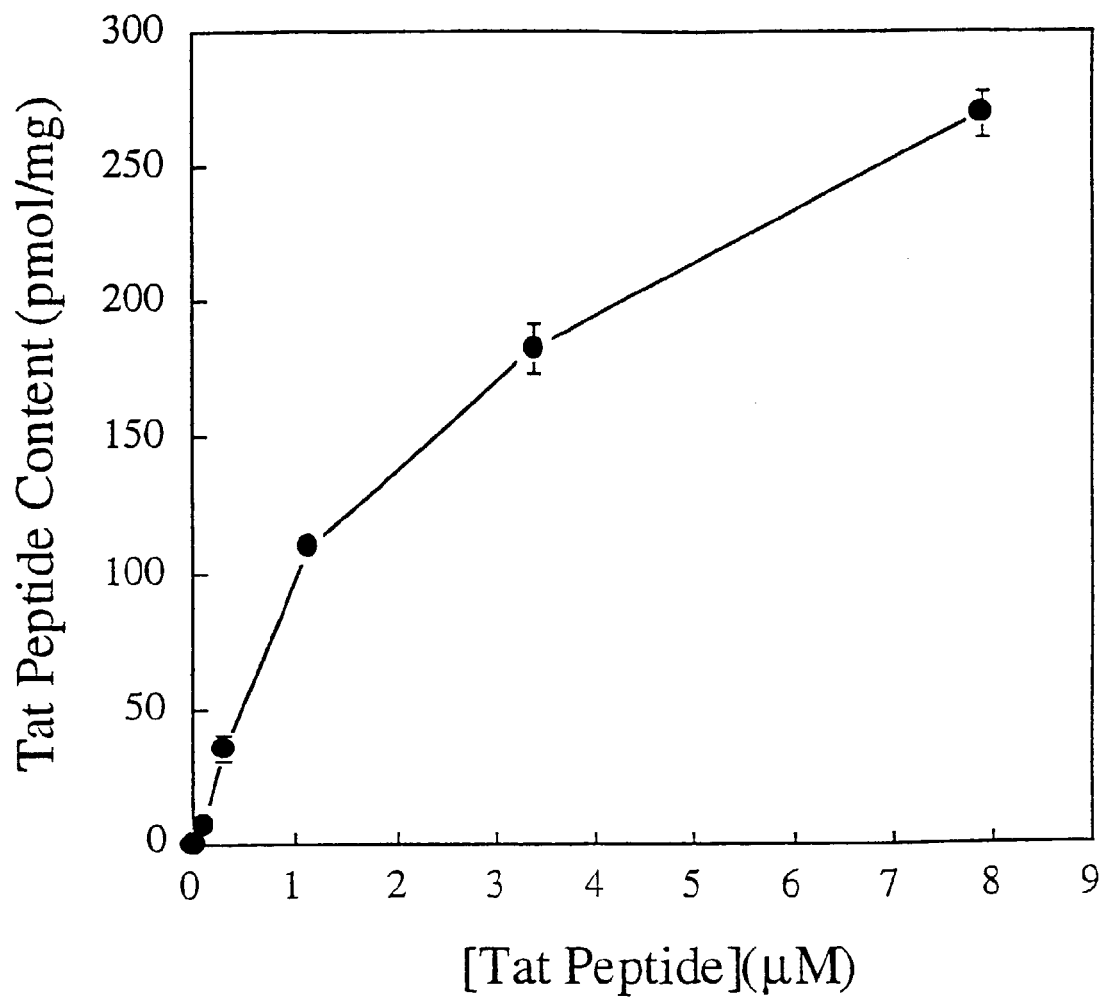
FIG. 4 shows the concentration-dependence of plateau accumulation of Tc-99m-Tat peptide conjugate into human Jurkat cells. Each point represents the mean of 4 observations±SEM when larger than the symbol.

To further characterize transport of the Tc-99m-Tat peptide metal complex, plateau accumulation of the agent in Jurkat cells after 10 minutes of incubation was determined as a function of extracellular concentration of the radiopharmaceutical. While readily detectable at concentrations as low as 7 nM, cell content of the Tat-complex showed evidence of concentration-saturation as extracellular concentrations rose into the range of 8 µM (FIG. 4). Curve fitting of the data suggested half-maximal accumulation of the complex occurred at ~3 µM.

To further define the interactions of the complexes with cells, Jurkat cells were incubated with Tc-99m-complexes in MEBSS buffer alone or buffer containing 130 mM K$^+$/20 mM Cl$^-$ and 1 µg/ml of the potassium ionophore valinomycin. Under these conditions, electrical potentials of the mitochondrial membrane ($\Delta\Psi$) and plasma membrane ($E_m$) are depolarized toward zero, eliminating the inward driving force for uptake of hydrophobic cationic or amphipathic molecules (Piwnica-Worms et al., *Circulation*, 82:1826-1838, 1990). However, while the complex might be characterized as amphipathic, net uptake of the complex under isoelectric conditions was not decreased compared to control buffer, suggesting that the mechanism of uptake was independent of membrane potential (data not shown).

Because several membrane permeant peptides have been reported to be accumulated within cells by mechanisms related to cytoskeletal function (Elliot and O'Hare, *Cell*, 88:223-233, 1997), several inhibitors known to impact microtubulin, actin microfilament and various cytoskeletal-mediated vesicular transport pathways were tested in Jurkat cell assays. Colchicine (100 ng/ml), taxol (1 µM), nocodozole (5 µg/ml), cytochalasin D (1 µM), brefeldin A (2.5 µg/ml) and wortmannin (100 nM) each had no significant effect on net cell uptake of this Tat-peptide metal complex, indicating that the pathway for accumulation of this agent is by a previously uncharacterized mechanism (data not shown). Furthermore, ice-cold buffer (4° C.) only modestly inhibited net accumulation of the complex, further pointing to a unique cell membrane translocation pathway not highly dependent on cellular metabolism.

Figure 5:
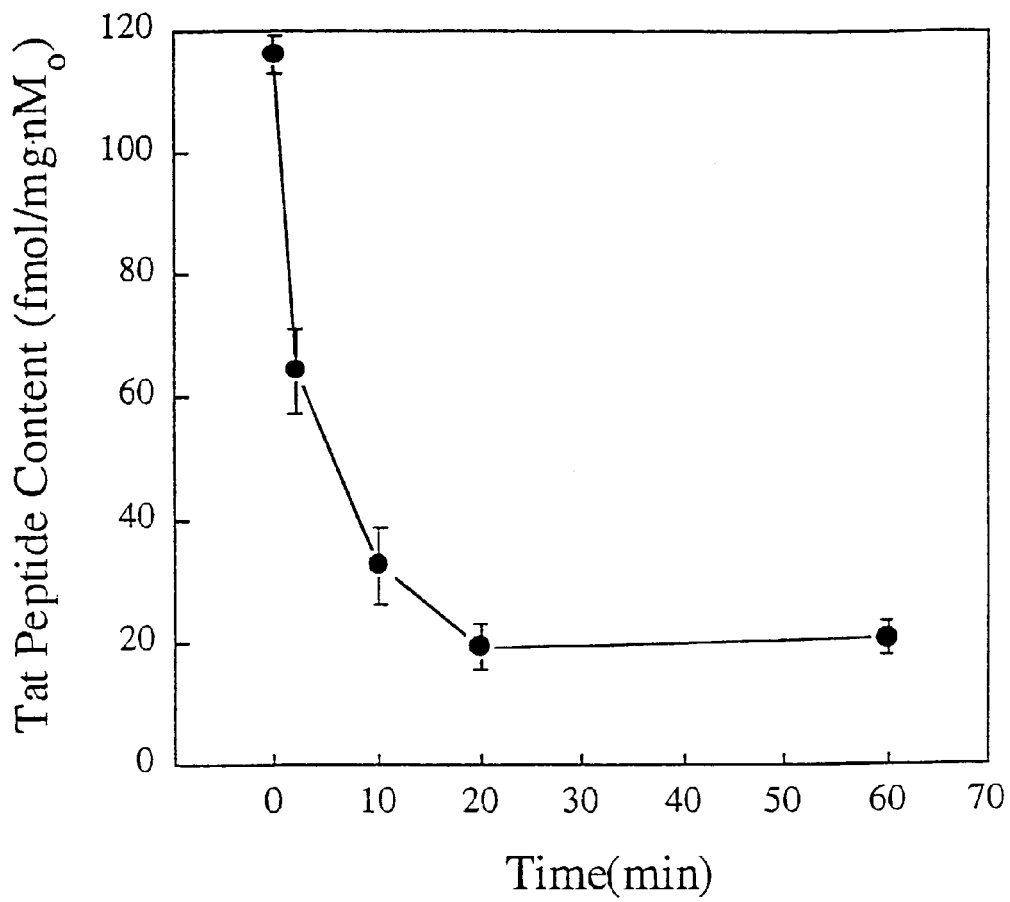
FIG. 5 shows washout kinetics of a non-functional Tc-99m-Tat peptide complex from human Jurkat cells. Cells were loaded to plateau uptake (~30 min), washed in ice cold buffer to clear extracellular spaces, and then bathed in isotope-free buffer at 37° C. for the times indicated. Cell-associated counts are shown. Each point represents the mean of 4 observations±SEM when larger than the symbol.

Cellular washout of the non-functional peptide complex of Example 2 which had been previously preloaded into Jurkat cells also showed very rapid kinetics. Washout was ~90% complete within 20 minutes (FIG. 5). This demonstrates that the majority of non-functionalized Tat peptide conjugate is not retained within cells when extracellular concentrations of the peptide are lowered. Only a residual level of peptide representing <10% of peak activity remained in a slowly exchanging or retaining compartment.

EXAMPLE 7

Fluorescence Microscopy

Exponentially growing human KB-8-5 epidermoid carcinoma cells on coverslips were rinsed in serum-free MEBSS (37° C.) followed by incubation in serum-free MEBSS containing the fluorescein labeled Tat-peptide conjugate (1 µM) at 37° C. for 15 min. Subsequently, cells on coverslips were fixed in 4% (v/v) formaldehyde in PBS at room temperature and then rinsed 3 times with PBS (1 min each). Cells were then stained and mounted with anti-fading mounting medium containing propidium iodide (1 µg/ml) following the recommended procedures of the manufacturer (Vectashield). The distribution of the fluorescence was analyzed on a Zeiss confocal laser fluorescence microscope equipped with a mercury lamp, oil immersion objectives and a CCD interfaced to a PC. Propidium iodide distribution was interrogated using 340-380 nm excitation and 430 nm emission, while fluorescein distribution was interrogated using 450-490 nm excitation and 520 nm emission.

Figure 6:
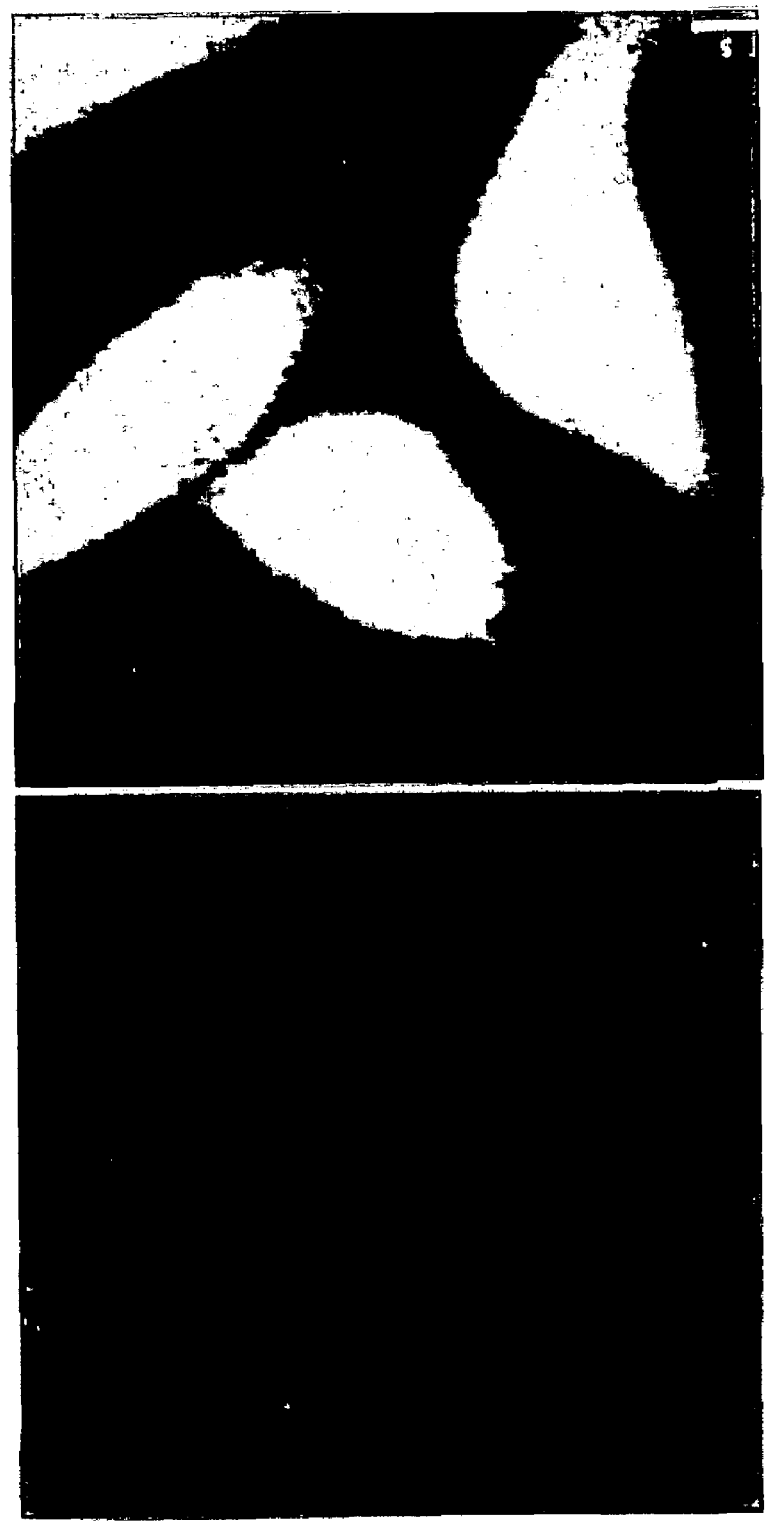
FIG. 6 shows the cellular accumulation of Tat peptide chelate conjugates in KB-3-1 human tumor cells. KB-3-1 cells were incubated with compound for 15 min at room temperature followed by a rapid wash and fixation: fluorescein maleimide (0.5 µM) alone (left) or Tat peptide chelate-fluorescein maleimide conjugate (right). Tat peptide chelate was conjugated with fluorescein maleimide on the C-terminal Cys residue. There was no counter staining of nuclei with propidium iodide in this example. Note the distribution of fluorescence from labeled peptide conjugate corresponding to cytosolic and nuclear (nucleolar) distribution. Bar=5 µm.

To localize the subcellular distribution of the Tat-peptide conjugate, uptake experiments were performed with the fluorescein derivatized conjugate using human KB-3-1 and KB-8-5 epidermoid carcinoma cells. Confocal microscopy revealed rapid cytoplasmic and nuclear accumulation of the fluorescein derivatized conjugate at 0.5 µM extracellular concentration of the agent. Both KB-3-1 cells (FIG. 6) and KB-8-5 cells (not shown) displayed a similar pattern and intensity of staining. Overall, the nuclear staining pattern of most fluorescent cells was suggestive of cytosolic and nucleolar localization of the peptide conjugate (FIG. 6).

EXAMPLE 8

Preparation of Caspase-3-Cleavable Metal and Fluorescein Conjugates

Caspase-3 cleavable Tat peptide conjugate was prepared by solid phase peptide synthesis using N-α-FMOC-protected amino acids and standard BOP/HOBt coupling chemistry as in Example 1. The peptide made incorporated a known caspase-3 cleavable sequence (DEVD) between the Tat peptide and the chelate. As described previously in Example 1, the peptide was amino acetylated, carboxy amidated and deprotected by standard methods. The peptide was purified (>94%) by preparative $C_{18}$ reversed-phase HPLC (see Example 1), and the identity of the peptide conjugate was confirmed by amino acid analysis and electrospray mass spectrometry (m/z: 2412.23; calc: $C_{96}H_{175}N_{43}O_{18}S_1$, 2411.79). The sequence was confirmed as acetyl-GRKKRRQRRR-GDEVDG-εKGC-amide (SEQ ID NO: 31).

The caspase-3 cleavable Tat peptide conjugate was labeled with Tc-99m by ligand exchange using Tc-99m-glucoheptonate as the ligand exchange reagent as described in Example 2. Radiochemical yield (>95%) of the oxotechnetium and purity (>90%) were determined by silica gel TLC using 15% TFA and radiometric detection (Bioscan). The (Tc-99m)-peptide complex showed an $R_f$=0.33, readily distinguished from (Tc-99m)-glucoheptonate ($R_f$=0.95) and (Tc-99m)-TcO$_4^-$ ($R_f$=0.95).

The caspase-3 cleavable Tat peptide was also readily complexed with Re by ligand exchange (Lister-James et al., *J. Nucl. Med.* 38:105-111, 1997). To 0.1 ml of a freshly prepared solution of glucoheptonate and reducing agent (200 mg (0.81 mmol) sodium α-D-glucoheptonate and 18.4 mg (0.082 mmol) tin(II) chloride dihydrate in 1 ml distilled water) was added 0.1 ml of a solution of ammonium perrhenate (14.9 mg (0.055 mmol) in 1 ml) and the mixture allowed to stand for 15 min at room temperature. To the mixture was added 1 mg of Tat peptide caspase-3 cleavable conjugate and the reaction allowed to proceed at room temperature for 30 minutes. The conjugate was purified by RP-HPLC as in Example 1. The identity of the ReO peptide conjugate was confirmed by electrospray mass spectrometry (m/z: 2612.0; calc: $C_{96}H_{172}N_{43}O_{19}S_1Re_1$, 2611.73).

RP-HPLC analysis using the same solvent gradient system and radiometric detection as previously described in Example 1 revealed two closely eluting peaks for the Tc-99m complex ($R_{t,1}$=23.9 min; $R_{t,2}$=25.8 min). RP-HPLC analysis and UV detection revealed two corresponding peaks for the Re complex ($R_{t,1}$=21.3 min; $R_{t,2}$=25.8 min), again consistent with formation of the expected isomers of the oxometal complexes.

The caspase-3 cleavable Tat peptide conjugate was also labeled at the C-terminal thiol of the peptide chelator with fluorescein maleimide using the same procedure as described in Example 3. The reaction was monitored by RP-HPLC at both 211 nm and 440 nm. The fluorescent peptide was purified by RP-HPLC ($R_t$=33.5 min; purity >97%) using the gradient conditions given in Example 3, and lyophilized in the dark. The identity of the desired fluorescein labeled peptide was confirmed by electrospray mass spectrometry (m/z: 2840.0).

EXAMPLE 9

Cleavage of the Caspase-3 Cleavable Linker In Vitro and In Situ

In small reaction vials, Tat peptide chelate as the fluorescein tagged conjugate of Example 8 was incubated with and without recombinant human active caspase-3 in commercially available reaction buffer (caspase buffer, Invitrogen). In vial 1 was peptide conjugate in buffer without caspase-3; in vial 2 was peptide conjugate with active caspase-3; and in vial 3 was stock peptide conjugate. After 6 hrs of incubation to assure completion of the reaction, the reaction mixtures were spotted at the origin of silica gel TLC plates, developed in 15% TFA, and analyzed under an UV lamp. While the unreacted peptide chelate stock and peptide chelate incubated in buffer alone retained an $R_f$=0.33, peptide chelate incubated in the presence of caspase-3 resulted in disappearance of the $R_f$=0.33 species and appearance of a peptide cleavage product with $R_f$=0.66. These data are consistent with cleavage of the Tat peptide conjugate at the D-G cleavage site, thereby releasing the small molecular weight C-terminus G-εKGC-fluorescein fragment identified near the solvent front on TLC. This represents direct evidence for successful synthesis of a caspase-3-cleavable Tat peptide imaging conjugate.

Figure 7:
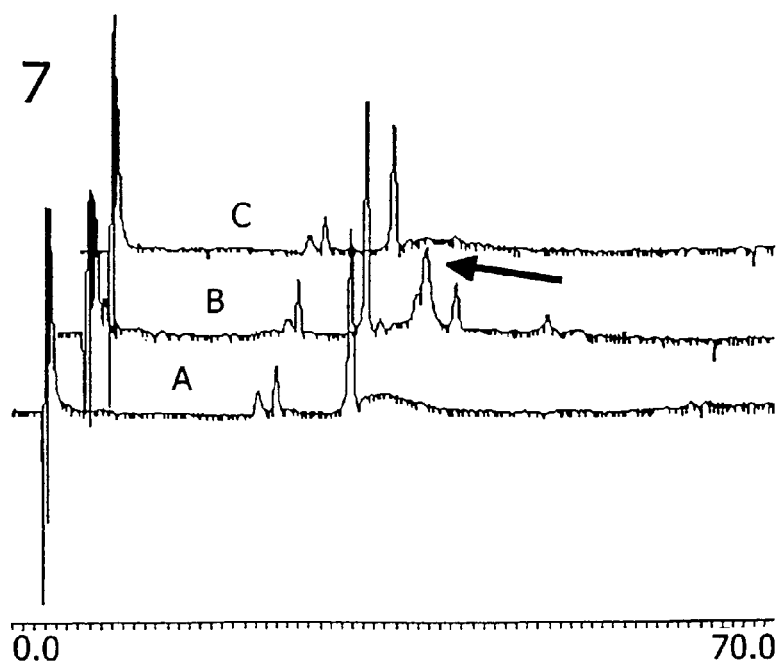
FIG. 7 shows RP-HPLC traces (440 nm) of cell lysates from control untreated Jurkat cells without added Tat peptide (A), untreated Jurkat cells incubated in fluorescein tagged Tat peptide (B), and ceramide-treated caspase-3 activated cells incubated in fluorescein tagged Tat peptide (C). The intact fluorescein tagged Tat peptide is seen in tracing B (arrow at $R_t$=33.5 min). In tracing C, note the absence of the intact Tat peptide. All three tracings show autofluorescent compounds present in the cells at $R_t$=22 and 28 min.

Human Jurkat leukemia cells express pro-caspase-3. Apoptosis can be induced by pre-incubation of Jurkat cells for 5 hr in medium containing C6-ceramide, a permeant phospholipid known to activate the cell death program (Herr, et al., *EMBO J* 16:6200-6208, 1997; Jayadev S, et al., *J Biol Chem* 270:2047-2052, 1995). After pre-incubation of Jurkat cells in MEBSS buffer at 370° C. in the absence (untreated) or presence of 5 µM C6-ceramide, 1 µM of the caspase-3 cleavable fluorescein tagged Tat peptide of Example 8 was added to the MEBSS buffer for 30 minutes. Untreated and apoptotic cells were then spun through oil (see Example 6) to clear extracellular spaces of Tat peptide, and the intact cells in the pellet were allowed to incubate for 5 minutes at 37° C. The oil was quickly suctioned off, the reaction terminated with cell lysis buffer (1% SDS, 10 mM sodium borate), and the cell extract centrifuged (500×g for 10 min) to pellet debris and precipitates. The supernatant was removed, lyophilized overnight, and resuspended in 500 µl of water. In untreated cell lysates, RP-HPLC analysis at 440 nm to observe fluorescein (see Example 3) showed the presence of a peak at $R_t$=33.5 min, consistent with parental Tat peptide conjugate (FIG. 7). In C6-ceramide-treated cells, however, no such species was observable (FIG. 7). These results demonstrate the rapid cleavage of the Tat-peptide conjugate comprising a caspase-3-reactive linker moiety in living cells upon activation of caspase-3.

The above experiment was repeated using the Tc-99m-Tat peptide of Example 8. Cells were treated as above except that the Tc-99m-Tat peptide was used, and there was no washout or post-incubation period. Tc99-m and protein content were determined using published methods (Bosch et al., *Leukemia* 11:1131-37, 1997). Cells induced to undergo apoptosis by treatment with C6-ceramide showed enhance uptake of Tc-99m, again showing that the presence of the caspase-3 cleavable linker resulted in identification of apoptotic cells.

EXAMPLE 10

Imaging Studies

FVB mice were anesthetized with metophane anesthesia. Tc-99m-Tat-peptide complex of Example 8 (125 µCi in 50 µl saline) was injected via a tail vein into mice positioned under a gamma scintillation camera (Siemens Basicam, Siemens Medical Systems, Iselin, N.J.; 5 mm pinhole collimator; 20% energy window centered over 140 keV photopeak of Tc-99m). Sequential posterior images of mice were collected at one frame/minute for 60 min with a 128×128 matrix and corrected for radioactive decay using a PC platform and standard commercial image analysis software. Accumulation of Tc-99m-Tat-peptide complex was analyzed by manually drawing regions-of-interest over various organs and subtracting background radioactivity determined from a region-of-interest placed adjacent to the thorax of each mouse. No corrections were made for scatter or attenuation. Whole body distribution of the complexes are presented in pseudo gray scale images with or without a saturation cutoff filter to highlight contrast differences in various organs.

Figure 8:
FIG. 8 shows scintigraphic image of rapid renal excretion of a Tc-99m-Tat peptide in a normal FVB mouse 30 minutes post injection. Following metofane anesthesia, Tc-99m-Tat chelate (200 µCi, prepared as described in the application) was administered by tail vein injection and the mouse immediately positioned for imaging on a gamma scintillation camera (Siemens Basicam; 5 mm pinhole collimator; 20% energy window centered over 140 keV). Sequential posterior images of the mouse were collected at one frame/minute for ~30 min with a 128×128 matrix. A [mal 5 minute acquisition with a 256×256 matrix was also obtained. Images were corrected for radioactive decay, but no corrections were made for scatter or attenuation. While radioactivity initially distributed throughout the body, note focal radioactivity within the urinary bladder after only 30 minutes, reflecting rapid renal excretion of the Tat peptide conjugate.

The Tc-99m-Tat peptide initially showed a whole body microvascular distribution, followed by rapid and abundant renal localization and excretion. By 30 minutes post injection of the imaging agent, the only site of imagable radioactivity was the urinary bladder (FIG. 8). There was a remarkable absence of liver activity or other background activity that would potentially interfere with the imaging of specific organ tissues or tumors. This rapid distribution pattern is consistent with the in vitro cell kinetic and localization data, but the rapidity of the renal excretion was unexpected.

Figure 9:
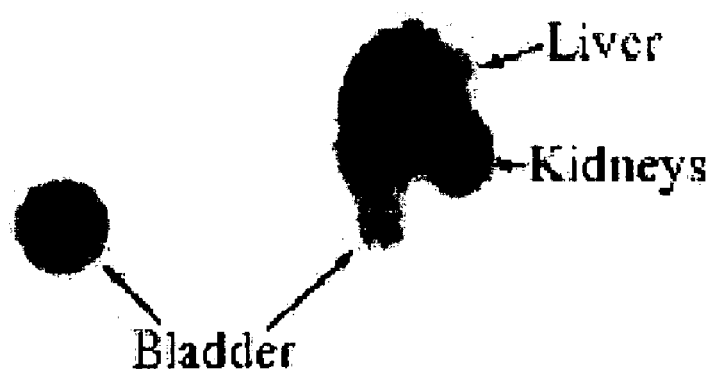
FIG. 9 shows scintigraphic images of organ distribution of caspase-3-cleavable Tc-99m-Tat peptide in FVB mice 30 minutes post injection. Using a published procedure (Blankenberg, et al., Proc Natl Acad Sci USA 95:6349-6354, 1998), FVB mice were administered purified hamster anti-Fas mAb (Jo2, PharMingen; 8 µg/animal) by i.v. injection and allowed to recover for 45 minutes prior to imaging. Following metofane anesthesia, Tc-99m-Tat chelate (200 µCi, prepared as described in the text) was administered by tail vein injection and mice immediately positioned for imaging on a gamma scintillation camera (Siemens Basicam; 5 mm pinhole collimator; 20% energy window centered over 140 keV). Sequential posterior images of mice were collected at one frame/minute for ~30 min with a 128×128 matrix. A final 5 minute acquisition with a 256×256 matrix was also obtained. Images were corrected for radioactive decay, but no corrections were made for scatter or attenuation. Left, untreated control mouse; right, mouse pre-treated with anti-Fag mAb. Note focal radioactivity only in the urinary bladder of the control mouse, but abundant retention of radioactivity in the pre-treated animal within the liver and kidneys, two organs that express the Fas receptor wherein caspase-mediated apoptosis is induced and imaged.

Next, direct demonstration of the feasibility of imaging caspase-3 activity in vivo in a living organism using gamma scintigraphy is shown. Massive hepatic apoptosis can be induced within 1-2 hours in mice following the intravenous injection of anti-Fas antibody (Ogasawara, et al., *Nature* 364:806-809; 1993; Blankenberg, et al., *Proc Natl Acad Sci USA* 95:6349-6354, 1998). The Fas receptor is expressed on liver, kidney, thymus, gonads and subsets of leukocytes (Ogasawara, et al., *Nature* 364:806-809; 1993). Thus, to test the specific localization of the caspase-3-cleavable Tc-99m-Tat peptide agent of Example 8 in organs undergoing apoptosis in vivo, a published procedure was used to image mice following the induction of apoptosis (Blankenberg, et al., *Proc Natl Acad Sci USA* 95:6349-6354, 1998). FVB mice were administered purified hamster anti-Fas mAb by i.v. injection and allowed to recover for 45 minutes prior to imaging. Following metofane anesthesia, 200 µCi of Tc-99m-Tat chelate was administered by tail vein injection, and mice were immediately positioned for imaging on a gamma scintillation camera. In untreated mice, the Tc-99m-Tat peptide initially showed a whole body distribution, followed by rapid and abundant renal localization and excretion, as expected. In contrast, mice pre-treated with anti-Fas mAb showed abundant hepatic and renal retention of radioactivity 30 minutes post injection, consistent with caspase-3-induced cleavage and retention of the imaging fragment within the target organs (FIG. 9, right). These images represent the first example of imaging caspase-3 activity in vivo, and demonstrate the utility of this approach in imaging with cell membrane-permeant peptide conjugates.

EXAMPLE 11

Preparation of D-Amino Acid Containing Peptide Conjugates

Peptide conjugates were prepared by solid state peptide synthesis as described in Example 1 using D N-α-FMOC-protected amino acids and standard BOP/HOBt coupling chemistry, except for the ε-Lys residue which used an N-α-tBOC, N-ε-FMOC-Lys to direct peptide coupling to the ε-amine. Some peptides were either N-terminus acetylated or biotinylated, and all peptides were C-terminus amidated and deprotected by standard methods. Peptides were purified by $C_{18}$ reversed-phase HPLC as described in Example 1. A single HPLC peak was observed for each peptide conjugate. The identity of the peptide conjugates was confirmed by amino acid analysis and electrospray mass spectrometry.

The following peptide conjugates were synthesized and characterized. The stereoisomeric identity of the membrane permeant peptide (Tat basic) domains and the chelation domains (εKGC) are indicated for each group. AHA represents aminohexanoic acid, an amino acid residue lacking a chiral center used in this example as a non-functional linker between the membrane permeant peptide and the metal chelation domains.

```
                    L            L
    Acetyl-GRKKRRQRRR-AHA-εKGC-amide     Conjugate 1    SEQ ID NO: 30
    Acetyl-RKKRRQRRR-AHA-εKGC-amide      Conjugate 2    SEQ ID NO: 32
    Biotin-RKKRRQRRR-AHA-εKGC-amide      Conjugate 3    SEQ ID NO: 32

L            D
    Acetyl-GRKKRRQRRR-AHA-εKGC-amide     Conjugate 4
    Acetyl-RKKRRQRRR-AHA-εKGC-amide      Conjugate 5
    NH₂-GRKKRRQRRR-AHA-εKGC-amide        Conjugate 6
    NH₂-RKKRRQRRR-AHA-εKGC-amide         Conjugate 7

D            D
    Acetyl-GRKKRRQRRR-AHA-εKGC-amide     Conjugate 8
    Acetyl-RKKRRQRRR-AHA-εKGC-amide      Conjugate 9
```

```
                                              -continued
NH₂-GRKKRRQRRR-AHA-εKGC-amide        Conjugate 10
NH₂-RKKRRQRRR-AHA-εKGC-amide         Conjugate 11

D              L
Acetyl-RKKRRQRRR-AHA-εKGC-amide      Conjugate 12
Biotin-RKKRRQRRR-AHA-εKGC-amide      Conjugate 13

D              D
Biotin-RAARRAARR-AHA-εKGC--amide     Conjugate 14
```

Additional examples of all D-amino acid sequences with favorable cell uptake and U/W ratios include arginine-rich sequences such as:

```
                                              (SEQ ID NO: 33)
acetyl-RKKRRNRRR-AHA-εKGC-amide (SEQ ID NO: 34)
acetyl-RKKRROmRRR-AHA-εKGC-amide (SEQ ID NO: 35)
acetyl-RKKRRERRR-AHA-εKGC-amide (SEQ ID NO: 36)
acetyl-RKKRRNorleuRRR-AHA-εKGC-amide
where Orn is ornithine and Norleu is norleucine.
```

EXAMPLE 12

Preparation of [99mTc$^V$O] Tat-Peptide Trifluroracetate

The Tat-peptide conjugates prepared in Example 11 were labeled with $^{99m}$Tc by ligand exchange using [$^{99m}$Tc] glucoheptonate as described in Example 2.

EXAMPLE 13

Preparation of [Re$^V$O] Tat-Peptide Trifluoroacetate

The Tat-peptide conjugates prepared in Example 11 were also reacted with Re by ligand exchange using [Re]glucohemtoanate as the ligand exchange reagent by the method used in Example 2. To 0.1 ml of a freshly prepared solution of 0.81 mmol sodium α-D-glucoheptonate and 0.082 mmol tin(II) chloride dihydrate was added 0.1 ml of a solution of 0.055 mmol ammonium perrhenate and the mixture allowed to stand for 15 minutes at room temperature. To the mixture was added 1 mg of the Tat-peptide conjugate (0.41 μmol) in water and the reaction allowed to proceed at room temperature for 30 minutes. Reversed phase HPLC analysis was performed as previously described and the desired fractions collected. The identity of the isolated [Re]Tat-peptide complexes was confirmed by electrospray mass spectrometry.

EXAMPLE 14

Cellular Uptake and Washout Studies of [$^{99m}$Tc] D-Tat-Peptide Conjugates

Control solution for the cellular uptake experiments was the modified Earle's balanced salt solution (MEBSS) described in Example 4.

Kinetic experiments of [$^{99m}$Tc]D-Tat-peptide complexes were performed in Jurkat leukemia cells suspended in MEBSS with minor modification of the methods described in Example 6. Transport experiments were performed in siliconized microfuge tubes and initiated by addition of 732.5 μl of cells at 2-3×10⁶ cells/ml to 10 μl of MEBSS containing [$^{99m}$Tc]D-Tat-peptide complex and 7.5 μl of vehicle alone or of any added drug in vehicle at 100 fold the desired concentration. Unless stated otherwise, [$^{99m}$Tc]D-Tat-peptide complex was added to MEBSS accompanied by a molar excess of unlabeled D-Tat-peptide as obtained directly from the labeling procedure. The final total peptide concentration was 7 nM to 8 μM (1-2 μCi/ml). The tube were incubated at 37° C. and the reaction terminated as previously described. For peptide washout experiments, cells were first incubated to plateau uptake (20 minutes) in MEBSS loading buffer at 37° C., collected by rapid centrifugation and the pellet resuspended in 50 ml of isotope-free MEBSS at 4° C. to clear extracellular tracer. Following another rapid spin, the cell pellet was resuspended in isotope-free MEBSS at 37° C. for various times and the reaction terminated as described previously. Protein assays and determination of gamma activity were as described in Example 6. Absolute concentration of total [Tc]Tat-peptide complex in solution was determined from the specific activity of Tc, based on equations of Mo/Tc generator equilibrium (Lamson et al., *J. Nucl. Med.*, 16:639-641, 1975). Transport data are reported as pmol of peptide$_i$(mg protein)$^{-1}$ (μM$_o$)$^{-1}$, wherein peptide$_i$ represents total peptide conjugate within the cells and (nM$^o$)$^{-1}$ represents concentration of total peptide conjugate in the extracellular buffer.

As shown in Table 1, stereoisomeric substitution of D amino acids in the metal chelation motif resulted in no significant change in overall accumulation levels in Jurkat cells. Neither deletion of the N-terminus Gly (Conjugates 5 and 7) nor deletion of the N-terminus acetyl (Conjugates 6 and 7) conferred any significant differences in overall cell penetration.

Conversely, peptide conjugates synthesized by solid phase methods with all D-amino acids comprising both the -εKGC chelation motif and the membrane permeant domain (Conjugates 8-11), showed an 8 to 9-fold increased accumulation. Again, neither deletion of the N-terminus Gly (Conjugates 9 and 11) nor deletion of the N-terminus acetyl (Conjugates 10 and 11) conferred any significant differences in the overall enhanced levels of cell penetration.

Figure 10:
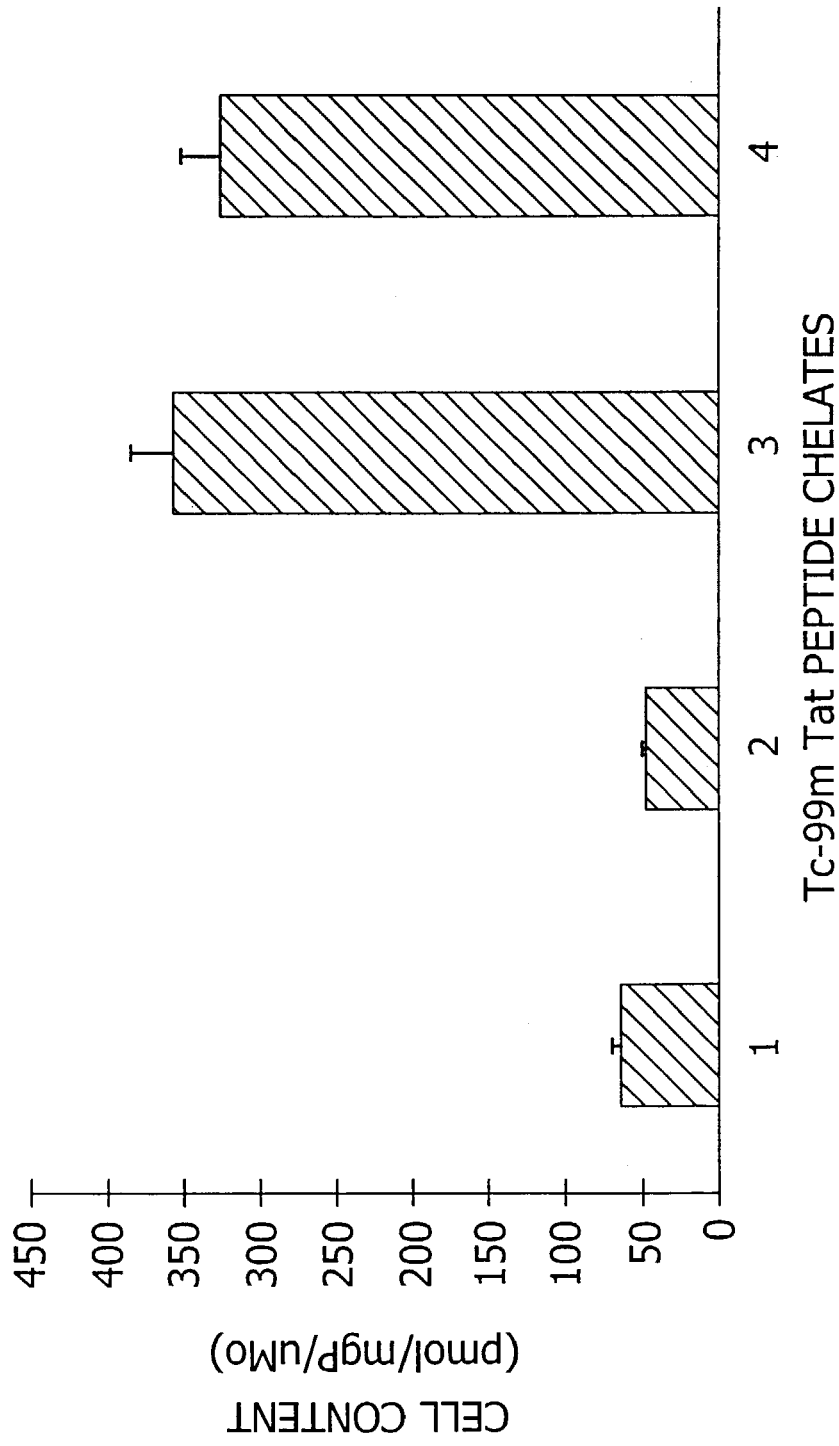
FIG. 10 shows comparative uptake of D, L and mixed D/L [$^{99m}$Tc]Tat-peptide chelate conjugates. Net, 20 minute accumulation values into Jurkat cells are shown. Each bar represents the mean of 4 observations+SEM. (1) L/L, [$^{99m}$Tc]Tat-peptide conjugate 2; (2) L/D [$^{99m}$Tc]Tat-peptide conjugate 5; (3) D/D [$^{99m}$Tc]Tat-peptide conjugate 9; and (4) D/L [$^{99m}$Tc]Tat-peptide conjugate 12.

Direct proof that this stereospecific enhancement of membrane penetration was conferred by the membrane permeant domain was obtained by synthesis of mixed peptides where natural L-amino acids comprised the -εKGC chelation motif and D-peptides comprised the membrane permeant domain (Conjugates 12 and 13). These mixed peptides also showed 8- to 9-fold increased accumulation in Jurkat cells (Table 1). Neither deletion of the N-terminus Gly (Conjugate 12) nor substitution of the N-terminus acetyl with biotin (Conjugate 13) conferred any significant differences in the overall enhanced levels of cell penetration. There was a minor trend for the D peptides to show slightly greater residual activity remaining within the cell 30 minutes after a wash in isotope-free buffer (Table 1). However, the net gain in cell uptake conferred by the D peptide permeation motif far exceeded this slight increase in residual binding as shown by the enhanced uptake/washout (U/W) ratios for the D peptides. Further demonstration of the importance of the specific D sequences indentified by these experiments is shown by comparison to another highly basic all D peptide (Conjugate 14). This all D peptide was no different than the native Tat peptide chelate (Conjugate 1) in overall cell uptake (Table 1). Direct comparative data of cell uptakes of peptide conjugates comprising various combination of stereoisomers of the permeation/chelation motifs (L/L; L/D; D/D; and D/L) are shown in FIG. 10. These data reinforce the large and unanticipated enhancement of cellular accumulation of [$^{99m}$Tc]Tat-peptide complexes conferred by the use of D-amino acids for synthesis of the membrane permeant domain.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims.

| Conjugate | # Amino Acids | N-term | Stereoisomer Tat Peptide Domain | Chelate Domain | 20 min Uptake | SEM | 30 min Washout | SEM | U/W Ratio |
|---|---|---|---|---|---|---|---|---|---|
| 1 | 14 | Ac, Gly | L | L | 77.93 | 3.47 | 24.26 | 7.63 | 3.2 |
| 2 | 13 | Ac | L | L | 61.73 | 6.05 | 10.99 | 1.84 | 5.6 |
| 3 | 13 | Biotin | L | L | 42.74 | 3.15 | 24.32 | 6.28 | 1.8 |
| 4 | 14 | Ac, Gly | L | D | 68.58 | 5.76 | 22.93 | 0.50 | 3.0 |
| 5 | 13 | Ac | L | D | 46.75 | 3.65 | 24.52 | 1.53 | 1.9 |
| 6 | 14 | Gly | L | D | 106.96 | 1.55 | 40.19 | 2.72 | 2.7 |
| 7 | 13 | | L | D | 64.35 | 1.63 | 26.84 | 2.52 | 2.4 |
| 8 | 14 | Ac, Gly | D | D | 317.92 | 21.29 | 50.87 | 14.76 | 6.2 |
| 9 | 13 | Ac | D | D | 357.91 | 28.00 | 42.99 | 2.01 | 8.3 |
| 10 | 14 | Gly | D | D | 314.02 | 61.48 | 55.67 | 1.59 | 5.6 |
| 11 | 13 | | D | D | 236.81 | 13.37 | 61.92 | 5.48 | 3.8 |
| 12 | 13 | Ac | D | L | 326.99 | 8.89 | 46.03 | 4.43 | 7.1 |
| 13 | 13 | Biotin | D | L | 387.25 | 24.42 | 36.22 | 5.16 | 10.7 |
| 14 | 13 | Biotin | D | D | 58.81 | 5.85 | 17.45 | 0.77 | 3.4 |

What is claimed is:

1. A method for delivering a pharmacologically active substance to a cell comprising,
   contacting the cell with an effective amount of a compound comprising:
   a cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36;
   a pharmacologically active substance; and
   a functional linker moiety linking the peptide and the pharmacologically active substance;
   wherein said functional linker moiety confers target cell specificity to the compound.

2. A method according to claim 1 wherein the pharmacologically active substance is a compound selected from the group consisting of: drugs, prodrugs, cytotoxic substances, enzymes, enzyme inhibitors, and bioactive substances.

3. A method according to claim 1 wherein the pharmacologically active substance is a drug selected from the group consisting of: chemotherapeutics, anti-inflammatories, antibiotics, antifungal agents, prostaglandins, steroids, anti-virals, monoclonal antibodies, immune adjuvants, and therapeutic radionuclides.

4. A method according to claim 3 wherein the pharmacologically active substance is a chemotherapeutic compound selected from the group consisting of: vinblastine, doxorubicin, bleomycin, methotrexate, 5-fluorouricil, 6-thioguanine, cytarabine, cyclophosphamide, taxol, taxotere, cis-platin, adriamycin, mitomycin, vincristine, UCN-01, acivicin, 9-aminocamptothecin, azacitidine, bromodeoxyuridine, bryostatin, carboplatin, dideoxyinosine, echinomycin, fazarabine, hepsulfam, homoharringtonine, iododeoxyuridine, leucovorin, merbarone, misonidazole, pentostatin, semustine, suramine, mephthalamidine, teroxirone, triciribine phosphate and trimetrexate.

5. A method according to claim 3 wherein the pharmacologically active substance is a chemotherapeutic compound selected from the group consisting of: vinblastine, doxorubicin, bleomycin, methotrexate, 5-fluorouricil, 6-thioguanine, cytarabine, cyclophosphamide, taxol, taxotere, cis-platin, adriamycin, mitomycin, and vincristine.

6. A method according to claim 3 wherein the pharmacologically active substance is an anti-inflammatory selected from the group consisting of: Celebrex, indomethacin, flurbiprofen, ketoprofen, ibuprofen and phenylbutazone.

7. A method according to claim 3 wherein the pharmacologically active substance is an antibiotic selected from the group consisting of: beta-lactams, aminoglycosides, macrolides, tetracyclines, pryridonecarboxylic acids and phosphomycin.

8. A method according to claim 2 wherein the pharmacologically active substance is an amino acid.

9. A method according to claim 8 wherein the amino acid is selected from the group consisting of: ascorbic acid and N-acetyltryptophan.

10. A method according to claim 2 wherein the bioactive substance is a vitamin.

11. A method according to claim 2 wherein the pharmacologically active substance is a bioactive substance selected from the group consisting of: ribozymes, granulocyte-stimulating factors, platelet-stimulating factors, erythrocyte-stimulating factors, macrophage-colony stimulating factors, interleukins, tumor necrosis factors, interferons, cytokines, monoclonal antibodies, immune adjuvants, gene therapy vectors, and growth factors.

12. A method according to claim 2 wherein the pharmacologically active substance is a drug comprising an antiviral compound selected from the group consisting of: AZT, DDI, acyclovir, gancyclovir, idoxuridine, amantadine and vidarabine.

13. A method according to claim 2 wherein the pharmacologically active substance is an enzyme selected from the group consisting of: transferases, hydrolyses, isomerases, proteases, ligases, kinases, oxidoreductases, esterases, phosphatases, glycosidases, and peptidases.

14. A method according to claim 2 wherein the pharmacologically active substance is an enzyme inhibitor selected from the group consisting of: leupeptin, chymostatin and pepstatin.

15. A method according to claim 2 wherein the pharmacologically active substance is a therapeutic radionuclide selected from the group consisting of: as I-123, I-125, I-130, I-131, I-133, Sc-47, As-72, Se-72, Y-90, Y80, Pd-100, Rh-100m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199.

16. A method according to claim 1 wherein said compound further comprises at least one D-amino acid.

17. A method according to claim 16 wherein the pharmacologically active substance is a compound selected from the group consisting of: drugs, prodrugs, cytotoxic substances, enzymes, enzyme inhibitors, and bioactive substances.

18. A method according to claim 16 wherein the pharmacologically active substance is a drug selected from the group consisting of: chemotherapeutics, anti-inflammatories, antibiotics, antifungal agents, prostaglandins, steroids, anti-virals, monoclonal antibodies, immune adjuvants, and therapeutic radionuclides.

19. A method according to claim 18 wherein the pharmacologically active substance is a chemotherapeutic compound selected from the group consisting of: vinblastine, doxorubicin, bleomycin, methotrexate, 5-fluorouricil, 6-thioguanine, cytarabine, cyclophosphamide, taxol, taxotere, cis-platin, adriamycin, mitomycin, vincristine, UCN-01, acivicin, 9-aminocamptothecin, azacitidine, bromodeoxyuridine, bryostatin, carboplatin, dideoxyinosine, echinomycin, fazarabine, hepsulfam, homoharringtonine, iododeoxyuridine, leucovorin, merbarone, misonidazole, pentostatin, semustine, suramine, mephthalamidine, teroxirone, triciribine phosphate and trimetrexate.

20. A method according to claim 18 wherein the pharmacologically active substance is a chemotherapeutic compound selected from the group consisting of: vinblastine, doxorubicin, bleomycin, methotrexate, 5-fluorouricil, 6-thioguanine, cytarabine, cyclophosphamide, taxol, taxotere, cis-platin, adriamycin, mitomycin, and vincristine.

21. A method according to claim 18 wherein the pharmacologically active substance is an anti-inflammatory selected from the group consisting of: Celebrex, indomethacin, flurbiprofen, ketoprofen, ibuprofen and phenylbutazone.

22. A method according to claim 18 wherein the pharmacologically active substance is an antibiotic selected from the group consisting of: beta-lactams, aminoglycosides, macrolides, tetracyclines, pryridonecarboxylic acids and phosphomycin.

23. A method according to claim 18 wherein the pharmacologically active substance is an amino acid.

24. A method according to claim 23 wherein the amino acid is selected from the group consisting of: ascorbic acid and N-acetyltryptophan.

25. A method according to claim 18 wherein the pharmacologically active substance is a vitamin.

26. A method according to claim 18 wherein the pharmacologically active substance is a bioactive substance selected from the group consisting of: ribozymes, granulocyte-stimulating factors, platelet-stimulating factors, erythrocyte-stimulating factors, macrophage-colony stimulating factors, interleukins, tumor necrosis factors, interferons, cytokines, monoclonal antibodies, immune adjuvants, gene therapy vectors, and growth factors.

27. A method according to claim 18 wherein the pharmacologically active substance is a drug comprising an antiviral compound selected from the group consisting of: AZT, DDI, acyclovir, gancyclovir, idoxuridine, amantadine and vidarabine.

28. A method according to claim 18 wherein the pharmacologically active substance is an enzyme selected from the group consisting of: transferases, hydrolyses, isomerases, proteases, ligases, kinases, oxidoreductases, esterases, phosphatases, glycosidases, and peptidases.

29. A method according to claim 18 wherein the pharmacologically active substance is an enzyme inhibitor selected from the group consisting of: leupeptin, chymostatin and pepstatin.

30. A method according to claim 18 wherein the pharmacologically active substance is a therapeutic radionuclide selected from the group consisting of: as I-123, I-125, I-130, I-131, I-133, Sc-47, As-72, Se-72, Y-90, Y-88, Pd-100, Rh-100m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199.

31. A method for delivering a pharmacologically active substance to a target cell comprising:
using a functional linker moiety to link the pharmacologically active substance to a cell-membrane permeant peptide to form a peptide conjugate,
wherein the cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36;
wherein the functional linker moiety is target cell-specific; and contacting the cell with an amount of the peptide conjugate.

32. A method according to claim 31 wherein the cell-membrane permeant peptide comprises at least one D-amino acid.

33. A method according to claim 31 wherein the pharmacologically active substance is selected from the group consisting of: drugs, prodrugs, cytotoxic substances, enzymes, enzyme inhibitors, and bioactive substances.

34. A method according to claim 31 wherein the pharmacologically active substance is a drug selected from the group consisting of: chemotherapeutics, anti-inflammatories, antibiotics, antifungal agents, prostaglandins, steroids, anti-virals, monoclonal antibodies, immune adjuvants, and therapeutic radionuclides.

35. A method according to claim 31 wherein the functional linker moiety comprises one of: an enzyme, a ribozyme, a low molecular weight peptide binding motif, a protein kinase consensus sequence, a protein phosphatase consensus sequence, or a protease-reactive sequence or a protease-specific sequence.

36. A method according to claim 31 wherein the functional linker moiety comprises a protease-reactive sequence or a protease-specific sequence, said method further comprising promoting release of the pharmacologically active substance from the peptide conjugate into the target cell through enzymatic action of the functional linker moiety on the peptide conjugate.

37. A method for delivering a pharmacologically active substance to a target cell comprising:
using a functional linker moiety to link the pharmacologically active substance to the amino-terminus or the carboxy-terminus of a cell-membrane permeant peptide to form a peptide conjugate,
wherein the cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36;
wherein the functional linker moiety is target cell-specific; and contacting the cell with an amount of the peptide conjugate.

38. A method according to claim 37 wherein the cell-membrane permeant peptide comprises at least one D-amino acid.

39. A method according to claim 37 wherein the pharmacologically active substance is a compound selected from the group consisting of: drugs, prodrugs, cytotoxic substances, enzymes, enzyme inhibitors, and bioactive substances.

40. A method according to claim 39 wherein the pharmacologically active substance is a drug selected from the group consisting of: chemotherapeutics, anti-inflammatories, antibiotics, antifungal agents, prostaglandins, steroids, anti-virals, monoclonal antibodies, immune adjuvants, and therapeutic radionuclides.

41. A method according to claim 37 comprising linking the pharmacologically active substance to the carboxy-terminus of the D-amino acid-containing, cell-membrane permeant peptide using an active ester of the pharmacologically active substance in the presence of a dehydrating agent.

42. A method according to claim 41 wherein the active ester of the pharmacologically active substance is a hemi-succinate ester of a compound selected from the group consisting of: N-hydroxysuccinimide, sulfo-N-hydroxy-succinimide, hydroxybenzotriazole, and p-nitrophenol.

43. A method according to claim 41 wherein the dehydration agent is selected from the group consisting of: dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI).

44. A method according to claim 1 for delivering a pharmacologically active substance to a target cell in vivo, the method further comprising:
combining the compound with a pharmaceutically acceptable carrier or diluent to form a pharmaceutical composition; and
and contacting the cell with the compound using a delivery route selected from the group consisting of the following: oral, parenteral, inhalation, rectal, intradermal, transdermal, and topical.

45. A method for delivering a pharmacologically active substance to a cell comprising:
contacting the cell with an effective amount of a compound comprising:
cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36;
a pharmacologically active substance; and
a functional linker moiety linking the peptide and the pharmacologically active substance;
wherein said functional linker moiety confers target cell specificity to the compound and the cell membrane permeant peptide and the functional linker form a peptide conjugate.

46. A method for delivering a pharmacologically active substance to a cell comprising:
contacting the cell with an effective amount of a compound comprising:
a cell-membrane permeant peptide with at least one D-amino acid the cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36;
a pharmacologically active substance; and
a functional linker moiety linking the peptide and the pharmacologically active substance;
wherein said functional linker moiety confers target cell specificity to the compound and the cell membrane permeant peptide and the functional linker form a peptide conjugate.

47. A method for delivering a pharmacologically active substance to a target cell comprising:
using a functional linker moiety to link the pharmacologically active substance to a cell-membrane permeant peptide to form a peptide conjugate; and
contacting the cell with an amount of the peptide conjugate;
wherein the functional linker moiety is target cell-specific and the cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36.

48. A method for delivering a pharmacologically active substance to a target cell comprising:
using a functional linker moiety to link the pharmacologically active substance to the amino-terminus or the carboxy-terminus of a cell-membrane permeant peptide to form a peptide conjugate; and
contacting the cell with an amount of the peptide conjugate;

wherein the functional linker moiety is target cell-specific and the cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36.

49. A method for delivering a pharmacologically active substance to a target cell comprising:
using a functional linker moiety to link the pharmacologically active substance to a cell-membrane permeant peptide to form a peptide conjugate,
wherein the functional linker moiety is target cell-specific and the cell-membrane permeant peptide consisting a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36; and
contacting the cell with an amount of the peptide conjugate.

50. A method for delivering a pharmacologically active substance to a target cell comprising:
using a functional linker moiety to link the pharmacologically active substance to the amino-terminus or the carboxy-terminus of a cell-membrane permeant peptide to form a peptide conjugate,
wherein the functional linker moiety is target cell-specific and cell-membrane permeant peptide consisting of a peptide sequence selected from the group consisting of SEQ ID NO: 30, SEQ ID NO: 31, SEQ ID NO: 32, SEQ ID NO: 33, SEQ ID NO: 34, SEQ ID NO: 35 and SEQ ID NO: 36.; and
contacting the cell with an amount of the peptide conjugate.

* * * * *

SEQUENCE LISTING

<160> NUMBER OF SEQ ID NOS: 36

<210> SEQ ID NO 1
<211> LENGTH: 16
<212> TYPE: PRT
<213> ORGANISM: Human immunodeficiency virus type 1

<400> SEQUENCE: 1

Arg Gln Ala Arg Arg Asn Arg Arg Arg Arg Trp Arg Glu Arg Gln Arg
1               5                   10                  15

<210> SEQ ID NO 2
<211> LENGTH: 19
<212> TYPE: PRT
<213> ORGANISM: Human T-cell lymphotropic virus type 1

<400> SEQUENCE: 2

Met Pro Lys Thr Arg Arg Arg Pro Arg Arg Ser Gln Arg Lys Arg Pro
1               5                   10                  15

Pro Thr Pro

<210> SEQ ID NO 3

-continued

```
<211> LENGTH: 16
<212> TYPE: PRT
<213> ORGANISM: Drosophila

<400> SEQUENCE: 3

Arg Gln Ile Leu Ile Trp Phe Gln Asn Arg Arg Met Lys Trp Leu Leu
1               5                   10                  15

<210> SEQ ID NO 4
<211> LENGTH: 30
<212> TYPE: PRT
<213> ORGANISM: Artificial
<220> FEATURE:
<223> OTHER INFORMATION: Peptide derivable from the heavy chain variable
      region of an anti-DNA monoclonal antibody

<400> SEQUENCE: 4

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 5
<211> LENGTH: 246
<212> TYPE: PRT
<213> ORGANISM: Herpes simplex virus

<400> SEQUENCE: 5

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Arg
145                 150                 155                 160

Ala Pro Thr Val Gln Leu Trp Gln Met Ser Arg Pro Arg Thr Asp Glu
                165                 170                 175

Asp Leu Asn Glu Leu Leu Gly Ile Thr His Arg Val Thr Val Cys Glu
            180                 185                 190

Gly Lys Asn Leu Leu Gln Arg Ala Asn Glu Leu Val Asn Pro Asp Val
        195                 200                 205

Val Gln Asp Val Asp Ala Ala Thr Ala Thr Arg Gly Arg Ser Ala Ala
    210                 215                 220

Ser Arg Pro Thr Glu Arg Pro Arg Ala Pro Ala Arg Ser Ala Ser Arg
225                 230                 235                 240
```

```
Pro Arg Arg Pro Val Glu
            245

<210> SEQ ID NO 6
<211> LENGTH: 36
<212> TYPE: PRT
<213> ORGANISM: Human immunodeficiency virus type 1

<400> SEQUENCE: 6

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 7
<211> LENGTH: 10
<212> TYPE: PRT
<213> ORGANISM: Human immunodeficiency virus type 1

<400> SEQUENCE: 7

Gly Arg Lys Lys Arg Arg Gln Arg Arg Arg
1               5                   10

<210> SEQ ID NO 8
<211> LENGTH: 7
<212> TYPE: PRT
<213> ORGANISM: Artificial sequence
<220> FEATURE:
<223> OTHER INFORMATION: protein binding motif
<220> FEATURE:
<221> NAME/KEY: MISC_FEATURE
<222> LOCATION: (3)..(3)
<223> OTHER INFORMATION: Unknown
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MISC_FEATURE
<222> LOCATION: (6)..(6)
<223> OTHER INFORMATION: Unknown

<400> SEQUENCE: 8

Arg Ser Xaa Ser Ser Xaa Pro
1               5

<210> SEQ ID NO 9
<211> LENGTH: 7
<212> TYPE: PRT
<213> ORGANISM: Artificial sequence
<220> FEATURE:
<223> OTHER INFORMATION: proetin binding motif
<220> FEATURE:
<221> NAME/KEY: VARIANT
<222> LOCATION: (3)..(3)
<223> OTHER INFORMATION: /F
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MISC_FEATURE
<222> LOCATION: (2)..(2)
<223> OTHER INFORMATION: Unknown
<220> FEATURE:
<221> NAME/KEY: MISC_FEATURE
<222> LOCATION: (4)..(4)
<223> OTHER INFORMATION: Unknown
```

```
<220> FEATURE:
<221> NAME/KEY: MISC_FEATURE
<222> LOCATION: (6)..(6)
<223> OTHER INFORMATION: Unknown

<400> SEQUENCE: 9

Arg Xaa Tyr Xaa Ser Xaa Pro
1               5

<210> SEQ ID NO 10
<211> LENGTH: 7
<212> TYPE: PRT
<213> ORGANISM: Artificial sequence
<220> FEATURE:
<223> OTHER INFORMATION: protein binding motif
<220> FEATURE:
<221> NAME/KEY: MOD_RES
<222> LOCATION: (5)..(5)
<223> OTHER INFORMATION: PHOSPHORYLATION

<400> SEQUENCE: 10

Arg Leu Ser His Ser Leu Pro
1               5

<210> SEQ ID NO 11
<211> LENGTH: 7
<212> TYPE: PRT
<213> ORGANISM: Artificial sequence
<220> FEATURE:
<223> OTHER INFORMATION: protein binding motif
<220> FEATURE:
<221> NAME/KEY: MOD_RES
<222> LOCATION: (1)..(7)
<223> OTHER INFORMATION: PHOSPHORYLATION

<400> SEQUENCE: 11

Arg Leu Tyr His Ser Leu Pro
1               5

<210> SEQ ID NO 12
<211> LENGTH: 7
<212> TYPE: PRT
<213> ORGANISM: Artificial sequence
<220> FEATURE:
<223> OTHER INFORMATION: protein binding motif
<220> FEATURE:
<221> NAME/KEY: MOD_RES
<222> LOCATION: (5)..(5)
<223> OTHER INFORMATION: PHOSPHORYLATION

<400> SEQUENCE: 12

Arg Leu Ser His Ser Leu Gly
1               5

<210> SEQ ID NO 13
<211> LENGTH: 5
<212> TYPE: PRT
<213> ORGANISM: Artificial sequence
<220> FEATURE:
<223> OTHER INFORMATION: Caspase-1 recognition site
<220> FEATURE:
<221> NAME/KEY: MISC_FEATURE
<222> LOCATION: (5)..(5)
<223> OTHER INFORMATION: Unknown

<400> SEQUENCE: 13

Tyr Glu Val Asp Xaa
1               5
```

```
<210> SEQ ID NO 14
<211> LENGTH: 6
<212> TYPE: PRT
<213> ORGANISM: Artificial sequence
<220> FEATURE:
<223> OTHER INFORMATION: Caspase-2 recognition site
<220> FEATURE:
<221> NAME/KEY: MISC_FEATURE
<222> LOCATION: (6)..(6)
<223> OTHER INFORMATION: Unknown

<400> SEQUENCE: 14

Tyr Asp Val Ala Asp Xaa
1               5

<210> SEQ ID NO 15
<211> LENGTH: 5
<212> TYPE: PRT
<213> ORGANISM: Artificial sequence
<220> FEATURE:
<223> OTHER INFORMATION: Caspase-3 recognition site
<220> FEATURE:
<221> NAME/KEY: MISC_FEATURE
<222> LOCATION: (5)..(5)
<223> OTHER INFORMATION: Unknown

<400> SEQUENCE: 15

Asp Glu Val Asp Xaa
1               5

<210> SEQ ID NO 16
<211> LENGTH: 5
<212> TYPE: PRT
<213> ORGANISM: Artificial sequence
<220> FEATURE:
<223> OTHER INFORMATION: Caspase-3 recognition site
<220> FEATURE:
<221> NAME/KEY: MISC_FEATURE
<222> LOCATION: (5)..(5)
<223> OTHER INFORMATION: Unknown

<400> SEQUENCE: 16

Asp Met Gln Asp Xaa
1               5

<210> SEQ ID NO 17
<211> LENGTH: 5
<212> TYPE: PRT
<213> ORGANISM: Artificial sequence
<220> FEATURE:
<223> OTHER INFORMATION: Caspase-4 recognition site
<220> FEATURE:
<221> NAME/KEY: MISC_FEATURE
<222> LOCATION: (5)..(5)
<223> OTHER INFORMATION: Unknown

<400> SEQUENCE: 17

Leu Glu Val Asp Xaa
1               5

<210> SEQ ID NO 18
<211> LENGTH: 5
<212> TYPE: PRT
<213> ORGANISM: Artificial sequence
<220> FEATURE:
<223> OTHER INFORMATION: Caspase-6 recognition site
<220> FEATURE:
<221> NAME/KEY: MISC_FEATURE
<222> LOCATION: (5)..(5)
<223> OTHER INFORMATION: Unknown
```

```
<400> SEQUENCE: 18

Val Glu Ile Asp Xaa
1               5

<210> SEQ ID NO 19
<211> LENGTH: 5
<212> TYPE: PRT
<213> ORGANISM: Artificial sequence
<220> FEATURE:
<223> OTHER INFORMATION: Caspase-7 recognition site
<220> FEATURE:
<221> NAME/KEY: MISC_FEATURE
<222> LOCATION: (5)..(5)
<223> OTHER INFORMATION: Unknown

<400> SEQUENCE: 19

Asp Glu Val Asp Xaa
1               5

<210> SEQ ID NO 20
<211> LENGTH: 5
<212> TYPE: PRT
<213> ORGANISM: Artificial sequence
<220> FEATURE:
<223> OTHER INFORMATION: Caspase-8 recognition site
<220> FEATURE:
<221> NAME/KEY: MISC_FEATURE
<222> LOCATION: (5)..(5)
<223> OTHER INFORMATION: Unknown

<400> SEQUENCE: 20

Ile Glu Thr Asp Xaa
1               5

<210> SEQ ID NO 21
<211> LENGTH: 5
<212> TYPE: PRT
<213> ORGANISM: Artificial sequence
<220> FEATURE:
<223> OTHER INFORMATION: Caspase-10 recognition site
<220> FEATURE:
<221> NAME/KEY: MISC_FEATURE
<222> LOCATION: (5)..(5)
<223> OTHER INFORMATION: Unknown

<400> SEQUENCE: 21

Ile Glu Ala Asp Xaa
1               5

<210> SEQ ID NO 22
<211> LENGTH: 14
<212> TYPE: PRT
<213> ORGANISM: Unknown organism
<220> FEATURE:
<221> NAME/KEY: MISC_FEATURE
<223> OTHER INFORMATION: Description of unknown organism:
      HIV p17-p24 A cleavage site

<400> SEQUENCE: 22

Ser Gln Val Ser Gln Asn Tyr Pro Ile Val Gln Asn Leu Gln
1               5                   10

<210> SEQ ID NO 23
<211> LENGTH: 14
<212> TYPE: PRT
<213> ORGANISM: Unknown organism
<220> FEATURE:
<221> NAME/KEY: MISC_FEATURE
```

```
<223> OTHER INFORMATION: Description of Unknown Organism:
      HIV p7-p1D cleavage site

<400> SEQUENCE: 23

Cys Thr Gl

```
<221> NAME/KEY: misc_feature
<222> LOCATION: (7)..(9)
<223> OTHER INFORMATION: n = a, t, c or g

<400> SEQUENCE: 28
tccagtnnna ctgga                                                        15

<210> SEQ ID NO 29
<211> LENGTH: 12
<212> TYPE: DNA
<213> ORGANISM: Unknown organism
<220> FEATURE:
<221> NAME/KEY: misc_feature
<223> OTHER INFORMATION: Description of unknown organism:
      thyroid hormone response element DNA recognition sequence

<400> SEQUENCE: 29
tccagtactg ga                                                           12

<210> SEQ ID NO 30
<211> LENGTH: 16
<212> TYPE: PRT
<213> ORGANISM: Artificial sequence
<220> FEATURE:
<223> OTHER INFORMATION: Tat peptide conjugate complex

<400> SEQUENCE: 30

Gly Arg Lys Lys Arg Arg Gln Arg Arg Arg Ala His Ala Lys Gly Cys
1               5                   10                  15

<210> SEQ ID NO 31
<211> LENGTH: 19
<212> TYPE: PRT
<213> ORGANISM: Artificial sequence
<220> FEATURE:
<223> OTHER INFORMATION: Caspase-3 cleavable Tat peptide conjugate

<400> SEQUENCE: 31

Gly Arg Lys Lys Arg Arg Gln Arg Arg Arg Gly Asp Glu Val Asp Gly
1               5                   10                  15

Lys Gly Cys

<210> SEQ ID NO 32
<211> LENGTH: 15
<212> TYPE: PRT
<213> ORGANISM: Artificial sequence
<220> FEATURE:
<223> OTHER INFORMATION: Tat peptide conjugate complex

<400> SEQUENCE: 32

Arg Lys Lys Arg Arg Gln Arg Arg Arg Ala His Ala Lys Gly Cys
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: A D-amino acid sequence of Tat peptide conjugate
      complex

<400> SEQUENCE: 33

Arg Lys Lys Arg Arg Asn Arg Arg Arg Ala His Ala Lys Gly Cys
1               5                   10                  15
```

-continued

```
<210> SEQ ID NO 34
<211> LENGTH: 15
<212> TYPE: PRT
<213> ORGANISM: Artificial sequence
<220> FEATURE:
<223> OTHER INFORMATION: A D-amino acid sequence of Tat peptide
      conjugate complex
<220> FEATURE:
<221> NAME/KEY: MISC_FEATURE
<222> LOCATION: (6)..(6)
<223> OTHER INFORMATION: Xaa = ornithine

<400> SEQUENCE: 34

Arg Lys Lys Arg Arg Xaa Arg Arg Arg Ala His Ala Lys Gly Cys
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: A D-amino acid sequence of Tat peptide
      conjugate complex

<400> SEQUENCE: 35

Arg Lys Lys Arg Arg Glu Arg Arg Arg Ala His Ala Lys Gly Cys
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: A D-amino acid sequence of Tat peptide
      conjugate complex
<220> FEATURE:
<221> NAME/KEY: MISC_FEATURE
<222> LOCATION: (6)..(6)
<223> OTHER INFORMATION: Xaa = norleucine

<400> SEQUENCE: 36

Arg Lys Lys Arg Arg Xaa Arg Arg Arg Ala His Ala Lys Gly Cys
1               5                   10                  15
```